US009155805B2

(12) United States Patent
Hamakubo et al.

(10) Patent No.: US 9,155,805 B2
(45) Date of Patent: Oct. 13, 2015

(54) MONOCLONAL ANTIBODY, AND USE THEREOF

(75) Inventors: Takao Hamakubo, Tokyo (JP); Yasuhiro Mochizuki, Tokyo (JP); Hiroyuki Aburatani, Tokyo (JP); Hiroko Iwanari, Tokyo (JP); Shunsuke Niwa, Tokyo (JP); Yoshiko Nakada, Tokyo (JP)

(73) Assignees: PERSEUS PROTEOMICS INC., Tokyo (JP); THE UNIVERSITY OF TOKYO, Tokyo (JP)

( * ) Notice: Subject to any disclaimer, the term of this patent is extended or adjusted under 35 U.S.C. 154(b) by 267 days.

(21) Appl. No.: 13/202,330

(22) PCT Filed: Feb. 20, 2010

(86) PCT No.: PCT/JP2010/001112
§ 371 (c)(1),
(2), (4) Date: Sep. 20, 2011

(87) PCT Pub. No.: WO2010/095461
PCT Pub. Date: Aug. 26, 2010

(65) Prior Publication Data
US 2012/0003149 A1  Jan. 5, 2012

(30) Foreign Application Priority Data

Feb. 20, 2009 (JP) ................... 2009-037341
Jun. 29, 2009 (JP) ................... 2009-153853

(51) Int. Cl.
| C07K 16/30 | (2006.01) |
| C12N 5/24 | (2006.01) |
| G01N 33/574 | (2006.01) |
| G01N 33/577 | (2006.01) |
| A61K 51/10 | (2006.01) |
| A61K 39/00 | (2006.01) |
| G01N 33/53 | (2006.01) |
| C07K 16/28 | (2006.01) |

(52) U.S. Cl.
CPC ............. *A61K 51/1072* (2013.01); *A61K 39/00* (2013.01); *A61K 51/106* (2013.01); *A61K 51/1054* (2013.01); *A61K 51/1057* (2013.01); *A61K 51/1063* (2013.01); *A61K 51/1066* (2013.01); *C07K 16/28* (2013.01); *C07K 16/30* (2013.01); *G01N 33/53* (2013.01); *C07K 2317/34* (2013.01); *C07K 2317/732* (2013.01); *G01N 33/574* (2013.01)

(58) Field of Classification Search
CPC . A61K 39/00; A61K 2039/505; C07K 16/28; C07K 16/30; C07K 2317/24; G01N 33/53; G01N 33/574
USPC ............ 530/350, 387.1, 387.3, 387.7, 387.9, 530/388.22, 388.8, 391.3, 391.7; 435/7.1, 435/7.23, 7.21, 334; 424/130.1, 133.1, 424/138.1, 143.1, 155.1
See application file for complete search history.

(56) References Cited

U.S. PATENT DOCUMENTS

| 2003/0113798 A1 * | 6/2003 | Burmer et al. ............... 435/7.1 |
| 2003/0124114 A1 | 7/2003 | McIntire |
| 2006/0153841 A1 | 7/2006 | Freeman |
| 2010/0111852 A1 | 5/2010 | Yoshida |

FOREIGN PATENT DOCUMENTS

| EP | 1074617 A2 * | 2/2001 |
| EP | 1900377 A1 * | 3/2008 |
| JP | 2003-507069 | 2/2003 |
| JP | 2005-500039 A | 1/2005 |
| WO | WO0109322 A1 * | 2/2001 |
| WO | WO02061087 A2 * | 8/2002 |
| WO | WO02083921 A2 * | 10/2002 |
| WO | WO02086443 A2 * | 10/2002 |
| WO | WO2004/082572 | 9/2004 |
| WO | WO2004082572 A2 | 9/2004 |
| WO | WO2005/073374 | 8/2005 |
| WO | WO2005073374 | 11/2005 |
| WO | WO2008/031842 | 3/2008 |
| WO | WO2008031842 | 3/2008 |
| WO | WO2008072723 | 6/2008 |
| WO | WO2008086342 A2 * | 7/2008 |
| WO | 2010095461 | 8/2010 |

OTHER PUBLICATIONS

Gugger et al. (Dis. Markers. 2008; 24 (1): 41-50).*
De Plaen et al. (Immunogenetics. 1994; 40: 360-369).*
Anderson et al. (J. Nucl. Med. Sep. 1992; 33 (9): 1685-91).*
T. Wittenberger et al, "An Expressed Sequence Tag (EST) Data Mining Strategy Succeeding in the Discovery of New G-Protein Coupled Receptors"; J. Mol.Biol. (2001) 307, 799-813.
K. Tabata et al, "The orphan GPCR GPR87 was deorphanized and shown to be a lysophosphatidic acid receptor"; Biochemical and Biophysical Research Communications 363 (2007) 861-866.
M. Gugger et al, "GPR87 is an overexpressed G-protein coupled receptor in squamous cell carcinoma of the lung"; Disease Markers 24 (2008) 41-50.
S. Glatt et al, "hGPR87 contributes to viability of human tumor cells"; Int. J. Cancer 122, 2008-2016 (2008).
K. Peachman et al, "Immunization with DNA through the skin"; Methods 31 (2003) 232-242.

(Continued)

*Primary Examiner* — Stephen Rawlings
(74) *Attorney, Agent, or Firm* — Jeffrey S. Melcher; Manelli Selter PLLC

(57) ABSTRACT

[Theme] To provide a monoclonal antibody against human GPR87. Also, to provide a novel means for diagnosing or treating a malignant tumor.
[Solution means] Monoclonal antibodies against human GPR87 are provided. The antibodies can recognize human GPR87, which is expressed on a cell membrane while retaining a three-dimensional structure, and can recognize GPR87, which is expressed in a cell endogenously with an epitope being present in an extracellular domain of full-length human GPR87. The antibodies are thus useful in biochemical analysis, etc., of GPR87, useful in immunohistological diagnosis, etc., of squamous cell carcinoma, and also potentially useful in PET diagnosis, antibodies for treatment, etc., of squamous cell carcinoma.

14 Claims, 5 Drawing Sheets

(56) References Cited

OTHER PUBLICATIONS

G. Galfre and C. Milstein, "Preparation of Monoclonal Antibodies:strategies and Procedures"; Methods in Enzymology 73 (1981) 3-46.

St. Groth et al, "Production of Monoclonal Antibodies: Strategy and Tactics"; Journal of Immunological Methods 35 (1980) 1-21.

S. L. Morrison et al, "Chimeric human antibody molecules: Mouse antigen-binding domains with human constant region domains"; Proc. Natl. Acad. Sci. USA 81 (1984) 6851-6855.

M. Verhoeyen et al, "Reshaping human antibodies: Grafting an antilysozyme activity"; Science 239 (1988) 1534-1536 10. RE Bird et al, "Single-chain antigen-binding proteins" Science 242 (1988) 423-426.

J. S. Huston et al, "Protein engineering of antibody binding sites: recovery of specific activity in an antidigoxin single-chain Fv analogue produced in *Escericia coli*"; Proc. Natl. Acad. Sci. USA 85 (1988) 5879-5883.

Anna M. Wu et al, "High-resolution microPET imaging of carcinoembryonic antigen-positive xenografts by using a copper-64-labeled engineered antibody fragment", Proc. Natl. Acad. Sci. USA 97 (2000) 8495-8500.

Manuel J. Koppe et al, "Antibody-guided radiation therapy of cancer", Cancer and Metastasis Reviews 24: 539-567, 2005.

Robert M. Sharkey et al, "Development of a Streptavidin-Anti-Carcinoembryonic Antigen Antibody, Radiolaveled Biotin Pretargeting Method for Radioimmunotherapy of Colorectal Cancer. Studies in a Human Colon Cancer Xenograft Model.", bioconjugate Chem. 1997, 8, 595-604.

R. Bird et al., Single-Chain Antigen_Binding Proteins; Science vol. 242, Reports, p. 423-426; Oct. 21, 1998.

Glatt, S, hGPR67 contributes to viability of human tumor cells; Int J. Cancer, 2008, vol. 122, p. 2008-2016, abstract, results.

\* cited by examiner

MONOCLONAL ANTIBODY, AND USE THEREOF

TECHNICAL FIELD OF THE INVENTION

The present invention relates to the monoclonal antibodies against human GPR87 (G protein-coupled receptor 87), methods for preparing them, hybridomas, tumor diagnostic agents, anti-tumor agents, the tumor diagnosis and treatment methods, use of the antibodies, etc.

BACKGROUND OF THE INVENTION

Malignant tumors (carcinoma, sarcoma and so on) are diseases which cause serious trouble with life maintenance of body and which have very high fatality rate when patients affect. In general they are classified by organs or tissues they develop from, into colon carcinoma, breast carcinoma, gastric carcinoma, lung carcinoma and bone sarcoma, for example. Histologically they are classified into adenocarcinoma, squamous cell carcinoma, transitional cell carcinoma, anaplastic carcinoma and so on.

Efficacious techniques for diagnosis and treatment against various types of malignant tumors have been developed by each research institution and the like. But valid techniques for diagnosis and treatment are not established in many cases.

Squamous cell carcinoma is a cancer which cells of squamous epithelium or squamous metaplasia are changed into malignant tumors. It appears at buccal cavity, tongue, vocal cord, esophagus, tracheobronchial region, lung, pharynx, larynx, female valuva, vagina, cervix, vaginal portion, skin, anus and so on. It occurs comparatively with increased frequency. For example, about 30% of lung carcinomas and about 90% of esophageal carcinomas are squamous cell carcinomas. Also about 80% of uterine carcinomas are cervical carcinomas and most of them are squamous cell carcinomas.

Transitional cell carcinoma is a cancer which cells derived from transitional epithelia tissues changed into malignant tumors. It appears at renal pelvis, urinary duct, bladder and so on.

Adenocarcinoma is a cancer which cells derived glandular tissues changed into malignant tumors. It appears at lacteal gland, stomach, colon, lung, gall bladder, bile duct, kidney, prostate, duodenum, pancreas, ovary, uterus, vagina and so on.

In skin cancer, basal cell carcinoma, squamous cell carcinoma and melanoma in turn appear with increased frequency. In head and neck cancer, most of tongue cancers are squamous cell carcinomas, in pharynx cancer, squamous cell carcinoma and malignant lymphoma appear with increased frequency, and most of larynx cancers are squamous cell carcinomas. In lung cancer, adenocarcinoma, squamous cell carcinoma, small cell carcinoma in turn appear with increased frequency. Most of esophaus cancers are squamous cell carcinomas, most of gastric cancers and colon cancers are adenocarcinomas, and most of pancreas cancers are tubular adenocarcinomas. Most of uterus cancers are adenocarcinomas, most of cervix cancers are squamous cell carcinomas, and most of breast cancers are adenocarcinomas. In kidney cancers, renal cell carcinomas (adenocarcinomas) and renal pelvis-ureter carcinomas (transitional cell carcinomas) in turn appear with increased frequency. Most of bladder cancers are transitional cell carcinomas and part of them are squamous cell carcinomas.

Each cancer is diagnosed by histopathological examination (biopsy, cytodiagnosis, tissue diagnosis, etc), CT (computerized tomography), PET (positron emission tomography), endoscopical ultrasonography and so on. However it is preferable to establish more accurate diagnostic techniques, for example, in regard to detection of with or without invasion and metastasis, and clarity of the cancerous or noncancerous boundaries. Also, operative therapy, chemical therapy or radiation therapy are treated for patients of each squamous cell carsinomas, but sufficient therapeutic effects have not been obtained in many cases.

GPCRs (G-protein-coupled receptors) are membrane proteins with seven transmembrane domeins, and are estimated to constitute a superfamily of nearly 1,000. Their ligands are diverse, for example, exogenous stimulations (lights, smells, tastes, pheromone, etc), lipids, hormones, autacoid, neurotransmitters, nucleotides and so on. In addition, it is thought that more than half of the drugs that are currently available act on GPCR.

GPR87 (G protein-coupled receptor 87) is a protein belonging to the GPCR family, its gene has homology with some of the P2Y receptor, but its function and other knowledge are poorly understood. In non-patent document 1, it was reported that the GPR87 gene has been identified by EST data mining. In non-patent document 1, it was reported that the ligand of GPR87 is lysophosphatidic acid.

It is known by microarray analysis that GPR87 has relatively high expression at the RNA transcriptional levels in skin and placenta of normal human tissues, in small airway epithelial cells, tracheal bronchial epithelial cells, epidermal keratinocytes and human prostate epithelial cells of normal human cells, in lung carcinomas (squamous cell carcinomas) and pancreatic carcinomas of cancer tissues, and cell lines derived from human esophageal carcinoma, cell lines derived from human gastric carcinoma, cell lines derived from human pancreatic carcinoma, cell lines derived from human lung carcinoma, cell lines derived from human ovarian carcinoma, and cell lines derived from human cervical carcinoma of carcinoma's cell lines.

In non-patent document 3, it was reported that GPR87 expresses highly in lung squamous cell carcinoma. In non-patent document 4, it was reported that GPR87 expresses in lung squamous cell carcinoma, lung adenocarcinoma, head and neck carcinoma, pharynx squamous cell carcinoma, larynx squamous cell carcinoma, skin squamous cell carcinoma and cervical squamous cell carcinoma, and it may contribute to viability of human tumor cells.

In patent document 1, GPR87 expression profiles obtained by real-time PCR are disclosed. In addition, the document mentions GPR87 monclonal antibodies, its chimeric antibodies, single chain antibodies and so on, however the actual establishment of hybridomas producing monoclonal antibodies has not been disclosed.

In patent document 2, the anti-GPR87 antibodies for the treatment of cancer are disclosed. In addition, the document mentions GPR87 monclonal antibodies, its modified antibodies, its chimeric antibodies, its humanized antibodies and so on, however only rabbit polyclonal antibodies have been produced and used by them, and the actual establishment of hybridomas producing monoclonal antibodies has not been disclosed.

To date, the anti-GPR87 antibody are sold by Acris Antibodies GmbH (German), Abcam, Inc. (UK), LifeSpan Biosciences, Inc. (USA), Novus Biologicals, LLC (USA), Thermo Fisher Scientific, Inc. (USA), MBL International Corporation (USA), Gene Tex, Inc. (USA), Genway Biotech, Inc. (USA), United States Biological (USA), Imgenex Corporation (USA) and so on. Some of these antibodies were used in the experiments mentioned in non-patent document 3 and non-patent document 4. However these antibodies are all rabbit polyclonal antibodies. To date, it is not reported that GPR87 monoclonal antibodies are actually created.

In non-patent document 5, it has been described about DNA immunization. In non-patent document 6 and 7, it has been described about examples of methods for producing monoclonal antibodies. In non-patent document 8, it has been described about chimera antibodies. In non-patent document 9, it has been described about humanized antibodies. In non-patent document 10 and 11, it has been described about scFv. Non-patent document 5-11 are incorporated into this application by reference. Citation of these documents is not an admission that any particular reference is prior art to this invention.

[Patent Document 1]

WO2004/082572

[Patent Document 2]

WO2008/031842

[Non-Patent Document 1]

T. Wittenberger et al, "An Expressed Sequence Tag (EST) Data Mining Strategy Succeeding in the Discovery of New G-Protein Coupled Receptors"; J. Mol. Biol. (2001) 307, 799-813

[Non-Patent Document 2]

K. Tabata et al, "The orphan GPCR GPR87 was deorphanized and shown to be a lysophosphatidic acid receptor"; Biochemical and Biophysical Research Communications 363 (2007) 861-866

[Non-Patent Document 3]

M. Gugger et al, "GPR87 is an overexpressed G-protein coupled receptor in squamous cell carcinoma of the lung"; Disease Markers 24 (2008) 41-50

[Non-Patent Document 4]

S. Glatt et al, "hGPR87 contributes to viability of human tumor cells"; Int. J. Cancer 122, 2008-2016 (2008)

[Non-Patent Document 5]

K. K. Peachman et al, "Immunization with DNA through the skin"; Methods 31 (2003) 232-242

[Non-Patent Document 6]

G. Galfre and C. Milstein, "Preparation of Monoclonal Antibodies: strategies and Procedures"; Methods in Enzymology 73 (1981) 3-46

[Non-Patent Document 7]

St. Groth et al, "Production of Monoclonal Antibodies: Strategy and Tactics"; Journal of Immunological Methods 35 (1980) 1-21

[Non-Patent Document 8]

S. L. Morrison et al, "Chimeric human antibody molecules: Mouse antigen-binding domains with human constant region domains"; Proc. Natl. Acad. Sci. USA 81 (1984) 6851-6855

[Non-Patent Document 9]

M. Verhoeyen et al, "Reshaping human antibodies: Grafting an antilysozyme activity"; Science 239 (1988) 1534-1536

[Non-Patent Document 10]

R E Bird et al, "Single-chain antigen-binding proteins" Science 242 (1988) 423-426

[Non-Patent Document 11]

J. S. Huston et al, "Protein engineering of antibody binding sites: recovery of specific activity in an antidigoxin single-chain Fv analogue produced in *Esericia coli*"; Proc. Natl. Acad. Sci. USA 85 (1988) 5879-5883

DISCLOSURE OF THE INVENTION

Object(s) of the Invention

Main objects of the present invention are to provide a monoclonal antibody against human GPR87, to provide a novel means for diagnosing or treating a malignant tumor, etc.

SUMMARY OF THE INVENTION

By performing immunization in mice by combining DNA immunization and cell immunization, the present inventors succeeded in establishing hybridomas that produce antibodies against human GPR87.

The present invention thus provides monoclonal antibodies against GPR87 (a protein having an amino acid sequence of sequence No. 1) or a protein having practically the same amino acid sequence as the above sequence or a partial peptide of either protein.

The inventors did not perform immunization using a partial peptide of GPR87 but performed immunization by DNA immunization and cell immunization. That is, immunization was performed with an antigen being expressed on a cell membrane. The antibodies can thus recognize GPR87, which is expressed on the cell membrane while retaining its three-dimensional structure.

Also, the present inventors performed immunization by DNA immunization and cell immunization with the antigen being expressed on the cell membrane. The antibodies can thus recognize not a transmembrane domain or an intracellular domain but an extracellular domain of full-length GPR87.

The present inventors also succeeded in preparing antibodies that can recognize not only a cell that is forced to express GPR87 but also GPR87 expressed endogenously in a cell, in other words, antibodies having a high affinity to the antigen.

Meanwhile, as a result of performing immunostaining of cancerous tissue sections, it was found that the antibodies can stain cancerous tissues of squamous cell carcinoma, transitional cell carcinoma, adenocarcinoma, etc., in a cancer-specific manner.

The antibodies according to the present invention are thus useful in biochemical analysis, etc., of GPR87, useful in immunohistological diagnosis, etc., of various carcinomas, and also potentially useful in PET diagnosis, antibody drugs, etc., for various carcinomas.

In addition, in comparison to polyclonal antibodies, monoclonal antibodies have such advantages as being high in antigen specificity due to an epitope being singular, being precisely definable in chemical structure, being capable of being mass produced at high purity with stability, being capable of being subject to antibody engineering, enabling mass production of engineered antibodies, etc.

EFFECT(S) OF THE INVENTION

By the present invention, monoclonal antibodies against human GPR87 can be provided.

BEST MODE(S) FOR CARRYING OUT THE INVENTION

<Amino Acid Sequence of GPR87>

A full-length amino acid sequence (358 amino acids) of GPR87 is shown in sequence No. 1. In the present invention, "GPR87" refers to a protein having an amino acid sequence that is the same as the amino acid sequence of sequence No. 1 and proteins having amino acid sequences that are practically the same as the amino acid sequence of sequence No. 1. Here, "practically the same" signifies that an amino acid sequence has a sameness of at least 80% and more preferably 90% or more.

GPR87 is a GPCR and is a seven-transmembrane protein. It thus has seven transmembrane domains, four extracellular domains, and four intracellular domains in its amino acid sequence.

Amino acid sequences of the four extracellular domains are shown in sequence Nos. 2 to 5 in an order starting from an N terminal side. The amino acid sequence of sequence No. 2 is the sequence of the extracellular domain closest to the N terminal side and is the sequence of the 1st to 41st amino acids in the full-length sequence. The amino acid sequence of sequence No. 3 is the sequence of the second extracellular domain from the N terminal side and is the sequence of the 101st to 118th amino acids in the full-length sequence. The amino acid sequence of sequence No. 4 is the sequence of the third extracellular domain from the N terminal side and is the sequence of the 182nd to 206th amino acids in the full-length sequence. The amino acid sequence of sequence No. 5 is the sequence of the fourth extracellular domain from the N terminal side and is the sequence of the 280th to 298th amino acids in the full-length sequence.

An amino acid sequence (15 amino acids) of sequence No. 6 is a portion included in the extracellular domain closest to the N terminal side and is the sequence of the 9th to 23rd amino acids of the full-length sequence.

<Monoclonal Antibodies and Methods for Manufacture Thereof According to the Present Invention>

In the present invention, "monoclonal antibodies against human GPR87" signifies isolated monoclonal antibodies that specifically bind with human GPR87 or with a protein having practically the same amino acid sequence as the sequence of human GPR87 or with a partial peptide of either protein and signifies engineered antibodies of the monoclonal antibodies and includes all of the above. Details of the engineered antibodies included in the present invention shall be described later.

Although the antibodies are not restricted more narrowly by properties, characteristics, etc., antibodies that can recognize GPR87, which is expressed on a cell membrane while retaining a three-dimensional structure, is more preferable in cases of use in biochemical analysis, tumor diagnosis, tumor treatment, etc.

Although an epitope of the antibody is not restricted in particular, it is more preferably present in an extracellular domain (in any one of the amino acid sequences of sequence Nos. 2 to 5) of full-length human GPR87 in cases of use in biochemical analysis, tumor diagnosis, tumor treatment, etc.

In cases of use in biochemical analysis, tumor diagnosis, tumor treatment, etc., the antibodies that can recognize not only a cell that is forced to express GPR87 but can also recognize GPR87 expressed endogenously in a cell and have a high affinity to an antigen are more preferable.

In cases of use in tumor treatment, etc., the antibodies having cellular cytotoxic activity, for example, ADCC activity (antibody-dependent cellular cytotoxic activity) or CDC activity (complement-dependent cytotoxic activity) are more preferable.

The antibodies are not particularly restricted in terms of class. For example, IgG, IgM, IgA, etc., are preferable and IgG is most preferable.

The antibodies are also not particularly restricted in terms of isotype. For example, IgG1, IgG3, IgG4, IgG2, etc., are preferable, and IgG1 is more preferable in terms of being highest in possibility of having ADCC activity or CDC activity.

Examples of the monoclonal antibodies according to the present invention include antibodies produced by hybridoma cell lines expressed by the following accession numbers.

Accession No. NITE BP-668 (depositary: Patent Microorganisms Depositary of the National Institute of Technology and Evaluation; address: 2-5-8 Kazusa Kamatari, Kisarazu City, Chiba Prefecture, Japan 292-0818; date of original deposition: Nov. 13, 2008), accession No. NITE BP-669 (depositary: Patent Microorganisms Depositary of the National Institute of Technology and Evaluation; address: 2-5-8 Kazusa Kamatari, Kisarazu City, Chiba Prefecture, Japan 292-0818; date of original deposition: Nov. 13, 2008), and accession No. NITE BP-673 (depositary: Patent Microorganisms Depositary of the National Institute of Technology and Evaluation; address: 2-5-8 Kazusa Kamatari, Kisarazu City, Chiba Prefecture, Japan 292-0818; date of original deposition: Nov. 13, 2008).

The antibody produced by the cell line of accession No. NITE BP-668 shall hereinafter be referred to as the "C0804 antibody," the antibody produced by the cell line of accession No. NITE BP-669 shall hereinafter be referred to as the "C0812 antibody," and the antibody produced by the cell line of accession No. NITE BP-673 shall hereinafter be referred to as the "C0815 antibody."

All of these antibodies can recognize human GPR87, which is expressed on a cell membrane while retaining the three-dimensional structure. Also, the epitopes of the antibodies are all present within an extracellular domain (an amino acid sequence of any one of sequence Nos. 2 to 5) of full-length human GPR87.

The C0804 antibody, the C0812 antibody, and the C0815 antibody can recognize not only a cell that is forced to express GPR87 but can also recognize GPR87 expressed endogenously in a cell and have a high affinity to the antigen.

All of the above antibodies have ADCC activity (antibody-dependent cellular cytotoxic activity; the same hereinafter).

CDR1, CDR2, and CDR3 amino acid sequences of an H chain of the C0804 antibody are shown in sequence Nos. 20, 21, and 22, respectively, and CDR1, CDR2, and CDR3 amino acid sequences of an L chain of the C0804 antibody are shown in sequence Nos. 23, 24, and 25, respectively.

CDR1, CDR2, and CDR3 amino acid sequences of an H chain of the C0812 antibody are shown in sequence Nos. 26, 27, and 28, respectively, and CDR1, CDR2, and CDR3 amino acid sequences of an L chain of the C0812 antibody are shown in sequence Nos. 29, 30, and 31, respectively.

CDR1, CDR2, and CDR3 amino acid sequences of an H chain of the C0815 antibody are shown in sequence Nos. 32, 33, and 34, respectively, and CDR1, CDR2, and CDR3 amino acid sequences of an L chain of the C0815 antibody are shown in sequence Nos. 35, 36, and 37, respectively.

The antibodies according to the present invention also broadly include modified antibodies with which the above antibodies are modified chemically or by genetic engineering. Examples of modifiers of the antibodies include various molecules, such as polyethylene glycol (PEG), avidin, streptavidin, biotin, etc., radioisotopes, fluorescing agents, enzymes, cytotoxins, anti-tumor agents, secondary antibodies modified by the above, etc. Antibody modification may be performed by a known method.

$^{18}$F, $^{15}$O, $^{13}$N, $^{11}$C, $^{82}$Rb, $^{68}$Ga, $^{198}$Au, $^{199}$Au, $^{32}$P, $^{32}$P, $^{125}$I, $^{131}$I, $^{123}$I, $^{90}$Y, $^{186}$Re, $^{188}$Re, $^{62}$Cu, $^{64}$Cu, $^{67}$Cu, $^{211}$At, $^{47}$Sc, $^{103}$Pb, $^{109}$Pb, $^{212}$, Pb, $^{71}$Ge, $^{77}$As, $^{105}$Rh, $^{113}$Ag, $^{119}$Sb, $^{121}$Sn, $^{131}$Cs, $^{143}$Pr, $^{161}$Tb, $^{177}$Lu, $^{191}$Os, $^{193}$Pt, $^{197}$Hg, etc., can be cited as examples of radioisotopes. A radioactive isotope may be bound to or made to modify an antibody directly or indirectly via a chelator, etc., using a known method.

A known chelator may be used as the chelator. For example, DTPA (diethylenetriamine pentaacetic acid), DOTA (1,4,7,10-tetraazacyclotetradecane-1,4,7,10-tetraacetic acid), DFO (deferoxamine), etc., may be used.

FITC (fluorescein isothiocyanate), rhodamine, phycoerythrin, phycocyanin, allophycocyanin, OPA (o-phthalaldehyde), fluorescamine, etc., can be cited as examples of fluorescing agents.

Horseradish peroxidase, β-galactosidase, luciferase, alkali phosphatase, etc., can be cited as examples of enzymes.

Diphtheria A-chain, Pseudomonas exotoxin A, pertussis toxin, ricin A chain, abrin a, modeccin toxin, α-sarcin, dianthin, curcin, crotin, gelonin, mitogellin, restrictocin, phenomycin, enomycin, tricothecene, trichosanthin, cytochalasin B, dihydroxyanthracenedione, mitoxantrone, emetine, colchicine, saporin, etc., can be cited as examples of cytotoxins.

The anti-tumor agent is not restricted in particular, and alkylating agents, antimetabolites, anti-tumor antibiotics, anti-tumor plant components, BRMs (biological response modifiers), angiogenesis inhibitors, cell adhesion inhibitors, matrix metalloprotease inhibitors, etc., can be cited as examples.

Chloroethylamine alkylating agents (nitrogen mustard, nitrogen mustard N-oxide, ifosfamide, melphalan, cyclophosphamide, chlorambucil, etc.), aziridine alkylating agents (carboqoune, thio-TEPA, etc.), epoxide alkylating agents (dibromomannitol, dibromodansitol, etc.), nitrosourea alkylating agents (carmustine, lomustine, semustine, nimustine hydrochloride, chlorozotocin, ranimustine, etc.), sulfonic acid esters (busulfan, inprosulfan tosylate, piposulfan, etc.), dacarbazine, procarbazine, etc., can be cited as examples of alkylating agents.

Purine antimetabolites (6-mercaptopurine, azathiopurine, 6-thioguanine, thioinosine, etc.), pyrimidine antimetabolites (fluorouracil, tegafur, tegafur-uracil, carmofur, doxifluridine, broxuridine, cytarabine, enocitabine, etc.), folate antimetabolites (methotrexate, trimetrexate, etc.), and salts and complexes thereof can be cited as examples of antimetabolites.

Anthracyclines (daunorubicin, aclarubicin, doxorubicin, pirarubicin, epirubicin, etc.), actinomycins (actinomycin D, etc.), chromomycins (chromomycin A3, etc.), mitomycins (mitomycin C, etc.), bleomycins (bleomycin, peplomycin, etc.), and salts and complexes thereof can be cited as examples of anti-tumor antibiotics.

Cisplatin, carboplatin, docetaxel, paclitaxel, gemcitabine, irinotecan, gefitinib, tamoxifen, L-asparaginase, aceglatone, schizophyllan, picibanil, ubenimex, krestin, and salts and complexes thereof can be cited as examples of other anti-tumor agents.

Plant alkaloids (camptothecin, vindesine, vincristine, vinblastine, etc.), epipodophyllotoxins (etoposide, teniposide, etc.), vinorelbine tartarate, and salts and complexes thereof can be cited as examples of anti-tumor plant components. Examples also include pipobroman, neocarzinostatin, and hydroxyurea.

Tumor necrosis factors, indomethacin, and salts or complexes thereof can be cited as examples of BRMs.

The type of antibodies (including engineered antibodies) according to the present invention is not restricted in particular, and mouse antibodies, human antibodies, rat antibodies, rabbit antibodies, lamb antibodies, camel antibodies, chicken antibodies, etc., are all included.

The antibodies (including engineered antibodies) according to the present invention may all be used for manufacture of anti-tumor agents.

An example of a method for preparing the monoclonal antibodies according to the present invention shall now be described. A method for preparing the engineered antibodies shall be described later.

The monoclonal antibodies may be prepared, for example, by procedures of (1) immunization of an animal, (2) establishment of hybridoma, (3) purification of antibody, etc.

(1) Immunization of an Animal

By performing immunization by a method that includes at least a procedure of performing at least one of either DNA immunization or cell immunization, an anti-GPR87 monoclonal antibody can be obtained efficiently in comparison to performing peptide immunization, etc.

A monkey, rabbit, dog, guinea pig, mouse, rat, sheep, goat, etc., can be cited as examples of an animal to be immunized and preferably, a mouse is used.

Principles, methods, etc., of DNA immunization are described, for example, in Non-Patent Document 5. For example, a gene gun is used to directly inject an expression vector incorporating human GPR87 into a subject animal subcutaneously or intracutaneously at a dosage of 0.01 to 100 μg per shot and approximately 5 to 30 shots are administered at intervals of 2 to 10 days to make an antigen be expressed within the animal and thereby achieve immunization.

The expression vector suffices to be a vector in which the human GPR87 gene can be incorporated and which expresses in animal cells, and known vectors may be employed. For example, plasmid vectors having an SRα promoter, SV40 promoter, LTR promoter, CMV promoter, HSV-TK promoter, CAG-promoter, etc., may be used. For example, a recombinant vector prepared by linking GPR87-encoding DNA to a downstream side of a promoter inside a suitable expression vector may be used.

Cell immunization is performed, for example, by establishing stable expression cells for human GPR87, diluting and suspending the cells at a suitable amount in PBS (phosphate-buffered saline), physiological saline, etc., and administering approximately 1 to 20 doses of the cells at approximately $1\times10^3$ to $1\times10^8$ cells per dose to a subject animal by tail vein administration or intraperitoneal administration. Also, after performing immunization by DNA immunization a plurality of times, a final immunization may be performed by cell immunization.

The cells suffice to be those that can express human GPR87 with stability, and known cells may be employed. For example, animal cells, such as COS-7 cells (monkey kidney derived cell line), Vero cells (African green monkey renal cell derived cell line), CHO cells (Chinese hamster ovary cell line), dhfr gene deficient CHO cells, mouse L cells, mouse 3T3 cells, AtT-20 cells (mouse pituitary derived cell line), ATDC5 cells (mouse chondroprogenitor cell line), mouse myeloma cells, HEK293 cells (human kidney derived cell line), FL cells (human amnion derived cell line), 293 cells, C127 cells (mouse fibroblast derived cell line), BALB3T3 cells (mouse fetus derived cell line), Sp-2/0 cells, GH3 cells (rat adenohypophysis cell derived cell line), Ba/F3 cells (mouse pro-B cell derived cell line), etc., may be used.

A human GPR87 stable expression cell line is established using any one of the above cells and used in cell immunization.

A known method may be used as a method for establishing the stable expression cells for human GPR87. For example, the stable expression cells for human GPR87 are established by introducing a human GPR87 expression vector in animal cells and performing drug selection, etc.

As a method for introducing the expression vector into the cells, a known method, such as a lipofection method, calcium phosphate method, electroporation method, etc., may be used. The same expression vectors as those mentioned above may be used.

The monoclonal antibodies according to the present invention are not restricted narrowly to those obtained by methods based on DNA immunization or cell immunization and broadly include those obtained by other known methods. Generally, a monoclonal antibody is prepared in many cases by performing immunization using a purified protein or synthetic peptide, etc. The present invention does not exclude monoclonal antibodies obtained by these methods. An example of a procedure for peptide immunization shall now be described.

First, an antigen (synthetic peptide) is diluted and suspended at a suitable amount in PBS (phosphate-buffered saline), physiological saline, etc., an appropriate amount of a normal adjuvant (for example, Freund's complete adjuvant, Freund's incomplete adjuvant, etc.) is mixed, and the mixture is emulsified and then administered a total of 2 to 10 times subcutaneously or intraperitoneally to a mammal at intervals of 4 to 21 days. Also, a suitable carrier may be used in the process of antigen immunization.

However, in comparison to other proteins, a hybridoma that produces a monoclonal antibody is difficult to prepare with a GPCR in many cases. The sequence of a GPCR is preserved among animal species and is readily tolerated immunologically and also, a GPCR is not readily recognized as an antigen because its three-dimensional structure is complex and unstable. Thus, in many cases, immunogenicity is weak when immunization is performed using a synthesized partial peptide of a GPCR. In addition, a GPCR is low in expression amount in comparison to other proteins, and it is thus difficult to obtain an antibody that recognizes a GPCR that is expressed endogenously in a cell and also difficult to construct a screening system for obtaining an intended antibody. The present inventors also attempted immunization using a synthetic peptide as the antigen but could not establish an antibody-producing hybridoma. In general with a GPCR, it is difficult to prepare a purified protein and in the case of the present invention, a purified protein is not necessarily suitable as an antigen.

On the other hand, a plurality of lines of antibody-producing hybridomas were successfully established by performing immunization by at least one of either DNA immunization or cell immunization. That is, in the case of the antibodies according to the present invention, an antibody-producing hybridoma can be obtained efficiently not by normal peptide immunization but by performing immunization by DNA immunization or cell immunization.

It is presumed that one of the reasons why the antibodies according to the present invention can be prepared comparatively efficiently by performing DNA immunization is as follows. As mentioned above, microarray analysis results show that GPR87 is highly expressed at the skin. In a case of performing DNA immunization by a gene gun, etc., the expression vector is shot directly into skin cells and GPR87 is made to be expressed on the cell membranes and used as the antigen. Thus, in the case of performing DNA immunization, GPR87 is readily expressed by the skin cells and immunization could thus be achieved efficiently.

(2) Establishment of Hybridoma

For example, after confirming that the antibody level in a serum of the animal has increased due to various immunizations, a final immunization is performed, a spleen or a lymph node of the immunized animal is collected 2 to 5 days after the final immunization, and the collected cells are fused with myeloma cells to prepare a monoclonal-antibody-producing hybridoma.

The cell fusion may be performed by a known method, for example, in accordance with methods described in Non-Patent Documents 6 and 7. For example, the antibody-producing cells (cells of the spleen, lymph node, etc.) collected from the immunized animal and the myeloma cells are mixed well at a proportion of approximately 1:1 to 10:1 in a culture medium, a PEG solution (for example, that of an average molecular weight of approximately 1,000 to 6,000) is heated to 37° C., the PEG is added to a concentration 30 to 60% (w/v) to both cells and mixed to fuse both cells. After then removing the PEG, the fused cells are sown at a predetermined concentration.

As mouse-derived myeloma cell lines, for example, P3 (P3-X63Ag8), P3U1 (P3-X63Ag8U1), X63.653 (X63Ag8.653), SP2 (Sp2/0-Ag14), FO, NS-1 (NSI/1-Ag4-1), NSO/1, FOX-NY, etc., are preferably used, and as rat-derived myeloma cell lines, for example, Y3-Ag1.2.3, YB2/0, IR983F, etc., are preferably used.

Next, for example, culturing is performed for several days to several weeks in a HAT selection medium (a culture medium containing hypoxanthine, aminopterin, and thymidine), etc., to kill cells besides the hybridoma and selectively culture the hybridoma.

The hybridoma that produces the intended antibody are then screened from the hybridomas surviving in the selection medium. The screening method is not restricted in particular and, for example, the intended hybridoma line may be selected by examining bonding or non-bonding of the antigen with the antibody in a supernatant of the hybridoma culture by a system for an ELISA method, flow cytometry method, Western blot method, dot blot method, radioimmunoassay method, etc. The hybridoma that produces the intended antibody is thus selected and then monocloned as necessary to establish the antibody-producing hybridoma.

(3) Purification of Antibody

The monoclonal antibody produced by the established hybridoma is recovered, separated, and purified.

The monoclonal antibody may be obtained from the hybridoma, for example, by culturing the established hybridoma and obtaining the antibody as a culture supernatant or by making the hybridoma proliferate by administration in a peritoneal cavity of a mammal and obtaining the antibody as a peritoneal fluid.

The separation and purification of the monoclonal antibody may be performed by a normal immunoglobulin separation and purification method.

The antibody may be separated and purified, for example, by a salting-out method, alcohol precipitation method, isoelectric precipitation method, electrophoresis method, adsorption and desorption method using an ion exchanger (for example, DEAE), ultracentrifugation method, gel filtration method, or method using an antigen-bound solid phase or activated adsorbent (protein A, protein G, etc.), etc.

<Engineered Antibodies According to the Present Invention and Method for Preparation Thereof>

In the present invention, "modified antibodies" signifies antibodies that are engineered while retaining amino acid sequences of CDRs (complementarity determining regions, the same holds hereinafter) of any one of the monoclonal antibodies against human GPR87 and antibody fragments that retain the CDR amino acid sequences and, for example, include all of chimeric antibodies, humanized antibodies, Fab antibody fragments, F(ab')$_2$ antibody fragments, Fab' antibody fragments, scFVs (single chain antibodies), dsFvs (disulfide-stabilized V region fragments), etc.

For example, in a case of an IgG antibody, two H chains (heavy chains) and two L chains (light chains) assemble to form a bilaterally symmetrical monomeric antibody molecule. Both the H chains and the L chains each have a V region (variable region, the same holds hereinafter) and a C region (constant region, the same holds hereinafter). The CDRs are regions in which the amino acid sequence changes at a high frequency and are present at three locations in the V region of each of the heavy and light chains (the V region of each H chain ($V_H$) and the V region of each L chain ($V_L$)). The amino acid sequences of the CDRs determine the antigen specificity. The portions of the V region besides the CDRs are referred to as the "framework regions."

A chimeric antibody is an engineered antibody having V regions derived from a mouse antibody and C regions derived from a human antibody.

The chimeric antibody may be prepared by a known technique based on sequence information of the H-chain V region and the L-chain V region. Gene fragments having base sequences that encode the H-chain V region amino acids of the antibody and gene fragments having base sequences that encode the L-chain V region amino acids are prepared. The V-region genes are linked with C-region genes of the human antibody to prepare a chimeric antibody gene. The chimeric antibody gene is linked with a suitable expression vector and introduced into culture cells. The culture cells are then cultured and the chimeric antibody may be obtained from the culture supernatant (see, for example, Non-Patent Document 8).

A humanized antibody is an antibody in which portions besides the CDRs are replaced by a human derived antibody. Besides the CDRs, portions of the amino acid sequences of the framework regions in the humanized antibody may be engineered (replaced, inserted, deleted, or added).

The humanized antibody may be prepared by a known technique based on sequence information of the H-chain CDRs and the L-chain CDRs. Gene fragments having base sequences encoding the H-chain CDR amino acids and gene fragments having base sequences encoding the L-chain CDR amino acids of an antibody of a mouse, etc., are prepared. The CDR genes are linked with the genes for the framework regions and the C regions of a human antibody to prepare the humanized antibody gene. The humanized antibody gene is linked with a suitable expression vector and introduced into culture cells. The culture cells are cultured and the humanized antibody may be obtained from the culture supernatant (see, for example, Non-Patent Document 9).

A source of the CDRs in the humanized antibody is not restricted in particular and the CDRs may be derived from any animal species. For example, the CDR sequences of a mouse antibody, rat antibody, rabbit antibody, or camel antibody, etc., may be used. Use of the CDR sequences of the mouse antibody is preferable in that the preparation of the monoclonal antibody is relatively easy in comparison to using the sequences of other animal species. For example, the humanized antibody may be prepared by a known technique using the CDR amino acid sequences of sequence Nos. 20 to 37 or the humanized antibody may be prepared by a known technique using the amino acid sequences of the CDRs and vicinities thereof of sequence Nos. 14 to 19.

A Fab antibody fragment is an antibody fragment, which, among fragments obtained by treatment of IgG with papain (proteolytic enzyme), has an antigen binding activity and in which approximately half of the H chain at the N terminal side and the entire L chain are bonded by disulfide bonds. The Fab antibody fragment may be obtained, for example, by treating an antibody according to the present invention with papain.

A F(ab')$_2$ antibody fragment is an antibody fragment, which, among fragments obtained by treatment of IgG with pepsin, has an antigen binding activity and in which Fab portions are bonded via disulfide bonds of a hinge region. it may be obtained, for example, by treating an antibody according to the present invention with pepsin.

A Fab' antibody fragment is an antibody fragment, which has an antigen binding activity and in which the disulfide bonds of the hinge region of the F(ab')$_2$ antibody fragment are severed. The Fab' antibody fragment may be obtained, for example, by treating the F(ab')$_2$ antibody fragment with the reducing agent, dithiothreitol.

The above antibody fragments may also be manufactured, for example, by inserting DNA that encodes the amino acid sequences of the antibody fragments in an expression vector for a prokaryotic organism or an expression vector for a eukaryotic organism and then introducing and making the vector express in the prokaryotic organism or eukaryotic organism.

An scFv (single chain Fv) is a single chain variable region fragment, which retains the property of binding with the antigen and in which a single heavy chain V region ($V_H$) and a light chain V region ($V_L$) are linked by a suitable peptide linker.

The scFv may be prepared by a known technique based on the sequence information of the H-chain CDRs and the L-chain CDRs, etc. For example, the scFv may be prepared by preparing a gene fragment having a base sequence that encodes the H-chain V region ($V_H$) amino acids of the antibody and a gene fragment having a base sequence that encodes the L-chain V region ($V_L$) amino acids, linking the two genes by a base sequence that encodes a peptide linker to construct DNA that encodes the scFv, inserting the DNA in an expression vector for a prokaryotic organism or an expression vector for a eukaryotic organism, and then introducing and making the expression vector express in the prokaryotic organism or eukaryotic organism (see, for example, Non-patent Documents 10 and 11).

A source of the CDRs in the scFv is not restricted in particular and the CDRs may be derived from any animal species. For example, the CDR sequences of a mouse antibody, rat antibody, rabbit antibody, or camel antibody, etc., may be used. Use of the CDR sequences of the mouse antibody is preferable in that the preparation of the monoclonal antibody is relatively easy in comparison to using the sequences of other animal species. For example, the scFv may be prepared by a known technique using the CDR amino acid sequences of sequence Nos. 20 to 37 or the scFV may be prepared by a known technique using the amino acid sequences of the CDRs and vicinities thereof of sequence Nos. 14 to 19.

In a dsFv (disulfide-stabilized V region fragment), polypeptides, respectively prepared by replacing a single amino acid residue in the H chain V region ($V_H$) or the L chain V region ($V_L$) by a cysteine residue, are bonded via a disulfide bond between the cysteine residues.

The dsFv may be prepared by a known technique based on the sequence information of the H-chain CDRs and the L-chain CDRs, etc. For example, the dsFv may be prepared by preparing a gene fragment having a base sequence that encodes the H-chain V region ($V_H$) amino acids of the antibody and a gene fragment having a base sequence that encodes the L-chain V region ($V_L$) amino acids and constructing DNA that encodes the disulfide-stabilized V region fragments, inserting the DNA in an expression vector for a prokaryotic organism or an expression vector for a eukaryotic organism, and then introducing and making the expression vector express in the prokaryotic organism or eukaryotic organism.

A source of the CDRs in the dsFv is not restricted in particular and the CDRs may be derived from any animal species. For example, the CDR sequences of a mouse antibody, rat antibody, rabbit antibody, or camel antibody, etc., may be used. Use of the CDR sequences of the mouse antibody is preferable in that the preparation of the monoclonal antibody is relatively easy in comparison to using the sequences of other animal species. For example, the dsFv may be prepared by a known technique using the CDR amino acid sequences of sequence Nos. 20 to 37 or the dsFV may be prepared by a known technique using the amino acid sequences of the CDRs and vicinities thereof of sequence Nos. 14 to 19.

The engineered antibodies according to the present invention broadly include modified antibodies prepared by modifying the engineered antibodies chemically or by genetic engineering in the same manner as described above. As modifiers of the antibodies, the same modifiers as those described above are all included. Modification of the antibodies may be performed by a known method.

<Biochemical Analyses According to the Present Invention>

The antibodies according to the present invention may be used in biochemical experiments, analyses, etc., using the antibodies.

Examples of known methods using the antibodies include immunostaining methods, immunohistological staining methods, ELISA (enzyme-linked immunosorbent assay) methods, ELISPOT (enzyme-linked immuno-spot) methods, Western blot methods, immunoprecipitation methods, flow cytometry methods, MACS (magnetic cell sorting) methods, affinity purification methods using the antibodies, etc. The antibodies according to the present invention have potential for use in such biochemical analyses.

<Medical Compositions According to the Present Invention>

Medical compositions according to the present invention suffice to contain at least any one of the antibodies described above.

Dosage forms of the medical compositions according to the present invention are not restricted in particular. For example, use may be made as a solid preparation (pill, capsule, granular agent, powdered agent, etc.) or as a liquid preparation (syrup, injectable agent, etc.).

In blending an antibody according to the present invention in a medical composition, a pharmacologically allowed carrier may be used. Any one of various organic and inorganic carrier substances that are commonly used as a pharmaceutical ingredient may be used as the carrier.

In the case of a solid preparation, for example, an excipient, lubricant, binding agent, disintegrating agent, etc., may be blended as appropriate with the antibody according to the present invention and its carrier. In the case of a liquid preparation, for example, a solvent, solubilizing agent, suspending agent, tonicity agent, buffering agent, soothing agent, etc., may be blended as appropriate with the antibody according to the present invention and its carrier. In addition, a preservative, antioxidant, colorant, sweetener, and other pharmaceutical additives may be appropriately blended as necessary.

As preferable examples of excipients, lactose, sucrose, D-mannitol, starch, crystalline cellulose, light anhydrous silicic acid, etc., may be used.

The medical compositions according to the present invention are potentially applicable to tumor diagnostic agents used in PET, anti-tumor agents, etc. The medical compositions are not narrowly restricted only to cases of use in such applications. That is, the present invention broadly includes cases of use in all other disorders.

<Tumor Diagnostic Agents and Tumor Diagnosis Methods According to the Present Invention>

As described above, the antibodies prepared by the present inventors can stain cancerous tissues of squamous cell carcinoma, transitional cell carcinoma, adenocarcinoma, etc., in a cancer-specific manner. The antibodies according to the present invention are thus potentially useful in tumor diagnosis.

For example, a tumor can possibly be detected and diagnosed by collecting a sample from a test subject, preparing a paraffin section or a frozen section, and performing immunohistological staining using a tumor diagnostic agent containing an antibody according to the present invention.

The sample may be obtained, for example, by sampling living tissue, expectorated sputum of a cancer patient, etc., by biopsy, etc., or by extracting cancerous tissue by cancer removal surgery, exploratory surgery, etc.

A tumor diagnostic agent according to the present invention suffices to contain an antibody according to the present invention and is not narrowly restricted by other components, etc. For example, a composition favorable for immunohistological staining, an antigen retrieval agent, an antibody stabilizer, etc., may be contained. The tumor diagnostic agent may be arranged in a kit together with reagents necessary for immunohistological staining, etc.

In a paraffin section or frozen section preparation procedure, immunohistological staining procedure, etc., known techniques may be used.

Tumor diagnosis according to the present invention is potentially applicable, for example, to skin cancers, head and neck cancers, lung cancers, esophageal cancers, cervical cancers, uterine cancers, pancreatic cancers, breast cancers, kidney cancers, ureteral cancers, and bladder cancers, and in particular to prickle cell carcinomas, basal cell carcinomas, or melanomas of skin, tongue cancers, squamous cell carcinomas or malignant lymphomas of the pharynx, squamous cell carcinomas of the larynx, squamous cell carcinomas or small cell carcinomas of the lung, squamous cell carcinomas of the esophagus, squamous cell carcinomas of the cervix, uterine adenocarcinomas, transitional cell carcinomas or squamous cell carcinomas of the bladder, transitional cell carcinomas of the renal pelvis or ureter, etc.

<Tumor Diagnostic Agents for PET and PET Diagnosis Methods According to the Present Invention>

The antibodies according to the present invention are potentially applicable to tumor diagnosis using PET (positron emission tomography).

As mentioned above, there is a high possibility that GPR87 is expressed specifically in a wide range of squamous cell carcinomas. Application to PET diagnosis may thus be possible by modifying an antibody according to the present invention by a radioisotope, administering the antibody into a body, and performing imaging, etc., by detecting the radiation by a PET apparatus. Also, PET diagnosis may possibly be performed by administering an antibody modified by biotin, etc., into a body in advance by a pretargeting method, thereafter administering avidin, etc., that has been modified by a radioisotope, and performing imaging, etc., by detecting the radiation by a PET apparatus.

Detection and imaging of tumor portions at high sensitivity by these methods provide possibilities for diagnoses of higher precision, such as clarification of presence or non-presence of infiltration or metastasis, clarification of boundaries of cancerous portions and non-cancerous portions, etc. There are also possibilities for improving tumor treatment results by combining with internal radiation therapy, external irradiation, ultrasonic treatment, thermotherapy, etc.

A tumor diagnostic agent for PET according to the present invention contains at least a composition with which any one of the above antibodies is modified by a radioisotope. Also, a tumor diagnostic agent for PET for use in the pretargeting method contains at least a composition with which any one of the above antibodies is modified with any one of various molecules such as biotin, etc.

As the antibody used in PET diagnosis, an antibody that can recognize human GPR87, which is expressed on a cell membrane while retaining the three-dimensional structure, and can recognize GPR87, which is expressed in a cell endogenously with the epitope being present in an extracellular domain (an amino acid sequence of any one of sequence Nos. 2 to 5) of full-length human GPR87, is preferable.

As the radioisotope used in PET diagnosis, a known radioisotope may be used and there are no restrictions in particular. $^{18}F$, $^{15}O$, $^{13}N$, $^{11}C$, $^{82}Rb$, $^{68}Ga$, $^{62}Cu$, $^{64}Cu$, $^{67}Cu$, etc., can be cited as examples of radioisotopes applicable to PET. In consideration of half-life, etc. $^{82}Rb$, $^{68}Ga$, and $^{64}Cu$ are preferable and $^{64}Cu$ is most preferable.

As mentioned above, the radioactive isotope may be bound to the antibody directly or indirectly via a chelator, etc., using a known method. As the chelator, the same as those mentioned above may be used, and for example, DTPA (diethylenetriamine pentaacetic acid), DOTA (1,4,7,10-tetraazacyclotetradecane-1,4,7,10-tetraacetic acid), etc., are preferable.

The dosage forms of the tumor diagnostic agents for PET according to the present invention are not restricted in particular. For example, use may be made as a solid preparation (pill, capsule, granular agent, powdered agent, etc.) or as a liquid preparation (syrup, injectable agent, etc.).

In blending a radiolabeled antibody according to the present invention in a tumor diagnostic agent for PET, a pharmacologically allowed carrier may be used in the same manner as described above. Also, in the same manner as described above, in the case of a solid preparation, for example, an excipient, lubricant, binding agent, disintegrating agent, etc., may be blended as appropriate with the antibody according to the present invention and its carrier. Likewise, in the case of a liquid preparation, for example, a solvent, solubilizing agent, suspending agent, tonicity agent, buffering agent, soothing agent, etc., may be blended as appropriate with the antibody according to the present invention and its carrier. In addition, a preservative, antioxidant, colorant, sweetener, and other pharmaceutical additives may be appropriately blended as necessary.

PET diagnosis according to the present invention is potentially applicable, for example, to skin cancers, head and neck cancers, lung cancers, esophageal cancers, cervical cancers, uterine cancers, pancreatic cancers, breast cancers, kidney cancers, ureteral cancers, and bladder cancers, and in particular to prickle cell carcinomas, basal cell carcinomas, or melanomas of skin, tongue cancers, squamous cell carcinomas or malignant lymphomas of the pharynx, squamous cell carcinomas of the larynx, squamous cell carcinomas or small cell carcinomas of the lung, squamous cell carcinomas of the esophagus, squamous cell carcinomas of the cervix, uterine adenocarcinomas, transitional cell carcinomas or squamous cell carcinomas of the bladder, transitional cell carcinomas of the renal pelvis or ureter, etc.

The tumor diagnostic agents for PET may be administered orally in the form of a pill, capsule (including soft capsules and microcapsules), powdered agent, granular agent, etc., or administered non-orally in the form of an injectable agent, suppository, pellet, etc. Forms of non-oral administration include intravenous, intramuscular, subcutaneous, intraorgan, intranasal, intracutaneous, ocular instillation, intracerebral, intrarectal, intravaginal, and intraperitoneal administration, administration into an interior of a tumor or a vicinity of a tumor, and direct administration to a focus.

Although differing according to administration route, symptoms, age, etc., an administration amount of a tumor diagnostic agent for PET according to the present invention is, for example, 0.001mg to 1,000 mg/kg×body weight per dose in a case of non-oral administration (intravenous administration, intramuscular administration, subcutaneous administration, etc.) and 0.001 mg to 1,000 mg/kg×body weight per day in a case of oral administration, and is preferably 0.001 mg to 1,000 mg/kg×body weight per dose by non-oral administration.

<Anti-Tumor Agents and Tumor Treatment Methods According to the Present Invention>

An anti-tumor agent according to the present invention suffices to contain at least any one of the antibodies (including engineered antibodies) according to the present invention.

As described above, in immunostaining of cancerous tissues, the antibodies prepared by the present inventors are capable of staining cancerous tissues of squamous cell carcinoma, transitional cell carcinoma, adenocarcinoma, etc., in a cancer-specific manner. The antibodies according to the present invention are thus potentially useful in tumor treatment as well.

As the antibody used in tumor treatment, an antibody that can recognize human GPR87, which is expressed on a cell membrane while retaining the three-dimensional structure, and can recognize GPR87, which is expressed in a cell endogenously with the epitope being present in an extracellular domain (an amino acid sequence of any one of sequence Nos. 2 to 5) of full-length human GPR87, is preferable.

As the antibodies used in tumor treatment, antibodies having cellular cytotoxic activity, for example, ADCC activity (antibody-dependent cellular cytotoxic activity) or CDC activity (complement-dependent cytotoxic activity) are more preferable. Even with an antibody that does not have cellular cytotoxic activity, it may be possible to obtain an anti-tumor effect by modification of the antibody with a radioisotope, a cytotoxic substance, an anti-tumor agent, etc. As examples of the modified antibodies, those described above may be applied.

The dosage forms of the anti-tumor agents according to the present invention are not restricted in particular. For example, use may be made as a solid preparation (pill, capsule, granular agent, powdered agent, etc.) or as a liquid preparation (syrup, injectable agent, etc.).

In blending an antibody according to the present invention in an anti-tumor agent, a pharmacologically allowed carrier may be used in the same manner as described above. Also, in the same manner as described above, in the case of a solid preparation, for example, an excipient, lubricant, binding agent, disintegrating agent, etc., may be blended as appropriate with the antibody according to the present invention and its carrier. Likewise, in the case of a liquid preparation, for example, a solvent, solubilizing agent, suspending agent, tonicity agent, buffering agent, soothing agent, etc., may be blended as appropriate with the antibody according to the present invention and its carrier. In addition, a preservative, antioxidant, colorant, sweetener, and other pharmaceutical additives may be appropriately blended as necessary.

The anti-tumor agents also include all anti-tumor agents that contain other active components, such as the other anti-tumor agents indicated as examples above, at the same time. For example, there is a possibility of obtaining an additive or synergistic anti-tumor effect by mixing and blending an anti-tumor agent according to the present invention with another anti-tumor agent.

The anti-tumor agents according to the present invention are potentially applicable, for example, to skin cancers, head and neck cancers, lung cancers, esophageal cancers, cervical cancers, uterine cancers, pancreatic cancers, breast cancers, kidney cancers, ureteral cancers, and bladder cancers, and in particular to prickle cell carcinomas, basal cell carcinomas, or melanomas of skin, tongue cancers, squamous cell carcinomas or malignant lymphomas of the pharynx, squamous cell carcinomas of the larynx, squamous cell carcinomas or small cell carcinomas of the lung, squamous cell carcinomas of the esophagus, squamous cell carcinomas of the cervix, uterine adenocarcinomas, transitional cell carcinomas or squamous cell carcinomas of the bladder, transitional cell carcinomas of the renal pelvis or ureter, etc.

The anti-tumor agents may be administered orally in the form of a pill, capsule (including soft capsules and microcapsules), powdered agent, granular agent, etc., or administered non-orally in the form of an injectable agent, suppository, pellet, etc. Forms of non-oral administration include intravenous, intramuscular, subcutaneous, intraorgan, intranasal, intracutaneous, ocular instillation, intracerebral, intrarectal, intravaginal, and intraperitoneal administration, administration into an interior of a tumor or a vicinity of a tumor, and direct administration to a focus.

Although differing according to administration route, symptoms, age, etc., an administration amount of an anti-tumor agent according to the present invention is, for example, 0.001 mg to 1,000 mg/kg×body weight per dose in a case of non-oral administration (intravenous administration, intramuscular administration, subcutaneous administration, etc.) and 0.001 mg to 1,000 mg/kg×body weight per day in a case of oral administration. For example, the above amount is administered in a single dose or in several doses.

The anti-tumor agents may be used solitarily or in combination with another anti-tumor agent, etc., in accordance with purpose, usage, symptom, etc. As the other anti-tumor agent, any one of those indicated above as examples may be used.

EXAMPLE 1

<Establishment of hGPR87 Stable Expression Cell Line>
In Example 1, a CHO cell line that expresses full-length human GPR87 with stability was established.

A cDNA clone of human GPR87 (made by Toyobo Co., Ltd.) was purchased, DNA with a FLAG tag sequence attached to the N terminal of the base sequence encoding GPR87 was prepared, and its sequence was inserted in a multicloning site of a pIRES-EGFP vector (made by Clontech Co.) to prepare an intended recombinant vector.

CHO cells were then transfected with the recombinant vector using Lipofect Amine 2000 (made by Invitrogen Corp.), selection was performed by adding G418 (made by Invitrogen Corp.) to a final concentration of 1 mg/mL, and cloning was performed by a limiting dilution method to establish a stable expression cell line. For the established cell line, the expression of EGFP was confirmed by a fluorescence microscope and Western blotting using an anti-FLAG antibody was performed to confirm the expression of human GPR87.

EXAMPLE 2

<Establishment of Hybridomas>
In Example 2, anti-GPR87-antibody-producing hybridomas were established.

DNA with an HA tag sequence attached to the N terminal of the base sequence encoding GPR87 was prepared and its sequence was inserted in a multicloning site of a pCXN2.1(−) vector to prepare a recombinant vector for DNA immunization.

DNA immunization of a mouse by the recombinant vector was then performed using a gene gun (trade name: "Helios Gene Gun" ("Helios" is a registered trademark), made by Bio-Rad Laboratories, Inc.). In accordance with an attached protocol, a cartridge was prepared so that the recombinant vector DNA amount was 1 μg/shot, 2 shots were administered in each immunization, and a total of 7 to 15 times of immunization was performed at intervals of almost 4 days.

Cell immunization was then performed using the GPR87 stable cell line prepared in Example 1. The cells were adjusted to a concentration of $1\times10^7$ cells/mL and 20 μL were tail-vein administered to mice (number of cells administered per mouse: $2\times10^5$ cells).

Next, 3 days after the cell immunization, the spleen was extracted from each immunized mouse, the spleen cells and myeloma cells (NS-1, purchased from Dainippon Pharma Co. Ltd.) were fused using polyethylene glycol, HAT selection was performed, and screening of the anti-GPR87-antibody-producing hybridoma was performed. For the screening, flow cytometry (by "FACSCalibur," made by Becton Dickinson, the same applies hereinafter) was performed using the human GPR87 stable cell line.

The lines that were positive in the screening were then monocloned and in a final stage, a plurality of anti-GPR87-antibody-producing hybridomas were established.

The deposited hybridoma lines are as follows:

(1) NITE BP-668

(2) NITE BP-669

(3) NITE BP-673

The respective hybridomas were then cultured, and using HPLC ("AKTA explore 100," made by Amersham Biosciences), the culture supernatants were purified by a protein G column ("Hi Trap Protein G HP," made by GE Healthcare) and then eluted with 100mM glycine (pH 2.7) to obtain respective purified antibodies.

In the following, (1) the antibody obtained from the NITE BP-668 cell line shall be referred to as the "C0804 antibody,"

(2) the antibody obtained from the NITE BP-669 cell line shall be referred to as the "C0812 antibody,"

(3) the antibody obtained from the NITE BP-673 cell line shall be referred to as the "C0815 antibody,"

and the antibodies obtained from other established hybridoma cell lines shall be referred to as the "C0806 antibody," "C0807 antibody," and "C0814 antibody," respectively.

EXAMPLE 3

<Examination of Antigen Specificities>

In Example 3, antigen specificities of the respective purified antibodies obtained in Example 2 were examined using flow cytometry.

The human GPR87 stable expression cell line established in Example 1 was sown in a 96-well plate at $1 \times 10^5$ cells/well, the respective purified antibodies were then added as primary antibodies at respective concentrations, and incubation at 4° C. was performed for 1 hour.

The supernatant was removed and after washing, a secondary antibody ("Alexa Fluor 647-R-phycoerythrin," made by Invitrogen Corp.) was added to a final concentration of 5 µg/ml and incubation at 4° C. was performed under protection from light for 30 minutes.

The supernatant was removed and after washing, adjustment with 1% BSA/PBS was performed and measurement by flow cytometry was performed.

The results of flow cytometry in the case of using the C0804 antibody are shown in FIG. 1A and FIG. 1B. In the present example, gating is not applied (the same hereinafter in the present example).

FIG. 1A shows the results of flow cytometry in the case of using the human GPR87 stable expression cell line established in Example 1, and FIG. 1B shows the results of flow cytometry in the case of using a wild cell line of CHO cells in place of the human GPR87 stable expression cell line (control).

In each figure, an abscissa indicates fluorescence intensity (logarithmic scale) and an ordinate indicates the number of cells emitting at each fluorescence intensity. In both figures, symbol 1 indicates the results of not adding the primary antibody (control), symbol 2 indicates the results of adding the primary antibody to a final concentration of 0.01 µg/mL, symbol 3 indicates the results of adding the primary antibody to a final concentration of 0.1 µg/mL, symbol 4 indicates the results of adding the primary antibody to a final concentration of 1 µg/mL, and symbol 5 indicates the results of adding the primary antibody to a final concentration of 10 µg/mL.

As shown in FIG. 1A and FIG. 1B, whereas in the case of using the human GPR87 stable expression cell line, the cell number of cells emitting fluorescence strongly was increased and the graphs of fluorescence intensity shifted to the right side in a concentration-dependent manner, such a shift was not observed in the case of using the wild cell line of CHO cells. This result indicates that the C0804 antibody binds specifically with human GPR87.

Flow cytometry measurements were made in the same manner for the respective antibodies of C0812, C0806, C0807, C0814, and C0815, and results similar to those of the C0804 antibody were obtained.

As measurement results of flow cytometry using the respective purified antibodies, geometric means of the fluorescence intensity are indicated below.

Results for the C0804 antibody in the case of using the hGPR87 stable expression cell line: Geometric mean when the primary antibody was not added: 18.36; geometric mean when the primary antibody concentration was 0.01 µg/mL: 28.93; geometric mean when the primary antibody concentration was 0.1 µg/mL: 109.98; geometric mean when the primary antibody concentration was 1 µg/mL: 577.66; and geometric mean when the primary antibody concentration was 10 µg/mL: 1238.62.

Results for the C0804 antibody in the case of using the CHO wild cell line:

Geometric mean when the primary antibody was not added: 4.73; geometric mean when the primary antibody concentration was 0.01 µg/mL: 4.49; geometric mean when the primary antibody concentration was 0.1 µg/mL: 4.51; geometric mean when the primary antibody concentration was 1 µg/mL: 4.48; and geometric mean when the primary antibody concentration was 10 µg/mL: 5.52.

Results for the C0812 antibody in the case of using the hGPR87 stable expression cell line: Geometric mean when the primary antibody was not added: 18.36; geometric mean when the primary antibody concentration was 0.01 µg/mL: 22.73; geometric mean when the primary antibody concentration was 0.1 µg/mL: 61.73; geometric mean when the primary antibody concentration was 1 µg/mL: 339.68; and geometric mean when the primary antibody concentration was 10 µg/mL: 1152.38.

Results for the C0812 antibody in the case of using the CHO wild cell line:

Geometric mean when the primary antibody was not added: 4.73; geometric mean when the primary antibody concentration was 0.01 µg/mL: 4.18; geometric mean when the primary antibody concentration was 0.1 µg/mL: 4.26; geometric mean when the primary antibody concentration was 1 µg/mL: 4.13; and geometric mean when the primary antibody concentration was 10 µg/mL: 4.85.

Results for the C0806 antibody in the case of using the hGPR87 stable expression cell line:

Geometric mean when the primary antibody was not added: 18.36; geometric mean when the primary antibody concentration was 0.01 µg/mL: 20.93; geometric mean when the primary antibody concentration was 0.1 µg/mL: 51.03; geometric mean when the primary antibody concentration was 1 µg/mL: 269.50; and geometric mean when the primary antibody concentration was 10 µg/mL: 910.21.

Results for the C0806 antibody in the case of using the CHO wild cell line:

Geometric mean when the primary antibody was not added: 4.73; geometric mean when the primary antibody concentration was 0.01 µg/mL: 4.26; geometric mean when the primary antibody concentration was 0.1 µg/mL: 4.35; geometric mean when the primary antibody concentration was 1 µg/mL: 4.27; and geometric mean when the primary antibody concentration was 10 µg/mL: 5.38.

Results for the C0807 antibody in the case of using the hGPR87 stable expression cell line:

Geometric mean when the primary antibody was not added: 18.36; geometric mean when the primary antibody concentration was 0.01 µg/mL: 19.02; geometric mean when the primary antibody concentration was 0.1 µg/mL: 38.41; geometric mean when the primary antibody concentration was 1 µg/mL: 143.13; and geometric mean when the primary antibody concentration was 10 µg/mL: 715.03.

Results for the C0807 antibody in the case of using the CHO wild cell line:

Geometric mean when the primary antibody was not added: 4.73; geometric mean when the primary antibody concentration was 0.01 µg/mL: 4.40; geometric mean when the primary antibody concentration was 0.1 µg/mL: 4.39; geometric mean when the primary antibody concentration was 1 µg/mL: 4.39; and geometric mean when the primary antibody concentration was 10 µg/mL: 5.52.

Results for the C0814 antibody in the case of using the hGPR87 stable expression cell line:

Geometric mean when the primary antibody was not added: 18.36; geometric mean when the primary antibody concentration was 0.01 µg/mL: 19.45; geometric mean when the primary antibody concentration was 0.1 µg/mL: 28.32;

geometric mean when the primary antibody concentration was 1 µg/mL: 102.77; and geometric mean when the primary antibody concentration was 10 µg/mL: 494.12.

Results for the C0814 antibody in the case of using the CHO wild cell line:

Geometric mean when the primary antibody was not added: 4.73; geometric mean when the primary antibody concentration was 0.01 µg/mL: 4.43; geometric mean when the primary antibody concentration was 0.1 µg/mL: 4.36; geometric mean when the primary antibody concentration was 1 µg/mL: 4.20; and geometric mean when the primary antibody concentration was 10 µg/mL: 4.80.

Results for the C0815 antibody in the case of using the hGPR87 stable expression cell line:

Geometric mean when the primary antibody was not added: 18.36; geometric mean when the primary antibody concentration was 0.01 µg/mL: 26.88; geometric mean when the primary antibody concentration was 0.1 µg/mL: 91.59; geometric mean when the primary antibody concentration was 1 µg/mL: 495.57; and geometric mean when the primary antibody concentration was 10 µg/mL: 1290.53.

Results for the C0815 antibody in the case of using the CHO wild cell line: Geometric mean when the primary antibody was not added: 4.73; geometric mean when the primary antibody concentration was 0.01 µg/mL: 4.38, geometric mean when the primary antibody concentration was 0.1 µg/mL: 4.41; geometric mean when the primary antibody concentration was 1 µg/mL: 4.29; and geometric mean when the primary antibody concentration was 10 µg/mL: 5.16.

EXAMPLE 4

<Examination of Whether or not Endogenously Expressed GPR87 can be Recognized>

In Example 4, flow cytometry was used to examine whether or not the respective purified antibodies obtained in Example 2 can recognize not only human GPR87 expressed in a forced expression system but can also recognize endogenously expressed human GPR87.

Me180 cells (cervical cancer cell line) were transfected with siRNA against human GPR87 (made by Invitrogen Corp., sequence No. 7) or a control siRNA (trade name: "Stealth RNAi Negative Universal Control LO," made by Invitrogen Corp.) and culturing was performed for 24 hours.

24 hours after the transfection, the cells were sown in a 96-well plate at $1 \times 10^5$ cells/well, the respective purified antibodies were then added as primary antibodies at respective concentrations, and incubation at 4° C. was performed for 1 hour.

The supernatant was removed and after washing, a secondary antibody ("Alexa Fluor 647-R-phycoerythrin," made by Invitrogen Corp.) was added to a final concentration of 5 µg/ml and incubation at 4° C. was performed under protection from light for 30 minutes.

The supernatant was removed and after washing, adjustment with 1% BSA/PBS was performed and measurement by flow cytometry was performed.

The results of flow cytometry in the case of using the C0804 antibody are shown in FIG. 2A and FIG. 2B. These are results of applying gating to living cells (the same hereinafter in the present example).

FIG. 2A shows the results of flow cytometry in the case of transfecting the Me180 cells with the control siRNA, and FIG. 2B shows the results of flow cytometry in the case of transfecting the Me180 cells with the siRNA against human GPR87 and suppressing the expression of human GPR87.

At the same time, an amount of expression of human GPR87 in ME180 cells was measured by real-time PCR, and the human GPR87 expression amount in the case of transfection with the siRNA against human GPR87 was found to be 5.9% of the case of transfection with the control siRNA. That is, by transfecting with the siRNA against human GPR87, the GPR87 expression amount could be suppressed at the RNA level to 5.9% of the normal state.

In each figure, the abscissa indicates the fluorescence intensity (logarithmic scale) and the ordinate indicates the number of cells emitting at each fluorescence intensity. In both figures, symbol 1 indicates the results of not adding the primary antibody (control), symbol 2 indicates the results of adding the primary antibody to a final concentration of 0.1 µg/mL, symbol 3 indicates the results of adding the primary antibody to a final concentration of 1 µg/mL, and symbol 4 indicates the results of adding the primary antibody to a final concentration of 10 µg/mL.

As shown in FIG. 2A and FIG. 2B, whereas in the case of the normal Me180 cells (the case of transfecting the Me180 cells with the control siRNA), the cell number of cells emitting fluorescence strongly was increased and the graphs of fluorescence intensity shifted to the right side in a concentration-dependent manner, the shift was suppressed in the case where the expression of human GPR87 is suppressed (the case of transfecting the Me180 cells with the siRNA against human GPR87). This result indicates that the C0804 antibody specifically binds with human GPR87 and the C0804 antibody can recognize not only human GPR87 expressed in a forced expression system but can also recognize endogenously expressed human GPR87.

Flow cytometry measurements were made in the same manner for the respective antibodies of C0812, C0806, C0807, C0814, and C0815, and results similar to those of the C0804 antibody were obtained.

As measurement results of flow cytometry using the respective purified antibodies, the geometric means of the fluorescence intensity are indicated below.

Results for the C0804 antibody in the case of using the control siRNA:

Geometric mean when the primary antibody was not added: 10.71; geometric mean when the primary antibody concentration was 0.1 µg/mL: 12.94; geometric mean when the primary antibody concentration was 1 µg/mL: 24.59; and geometric mean when the primary antibody concentration was 10 µg/mL: 63.47.

Results for the C0804 antibody in the case of using the siRNA against GPR87:

Geometric mean when the primary antibody was not added: 10.16; geometric mean when the primary antibody concentration was 0.1 µg/mL: 10.26; geometric mean when the primary antibody concentration was 1 µg/mL: 12.95; and geometric mean when the primary antibody concentration was 10 µg/mL: 20.57.

Results for the C0812 antibody in the case of using the control siRNA:

Geometric mean when the primary antibody was not added: 10.71; geometric mean when the primary antibody concentration was 0.1 µg/mL: 11.31; geometric mean when the primary antibody concentration was 1 µg/mL: 16.87; and geometric mean when the primary antibody concentration was 10 µg/mL: 37.10.

Results for the C0812 antibody in the case of using the siRNA against GPR87:

Geometric mean when the primary antibody was not added: 10.16; geometric mean when the primary antibody concentration was 0.1 µg/mL: 9.67; geometric mean when the primary antibody concentration was 1 µg/mL: 10.23; and geometric mean when the primary antibody concentration was 10 µg/mL: 11.34.

Results for the C0806 antibody in the case of using the control siRNA:
Geometric mean when the primary antibody was not added: 10.71; geometric mean when the primary antibody concentration was 0.1 µg/mL: 11.03; geometric mean when the primary antibody concentration was 1 µg/mL: 11.89; and geometric mean when the primary antibody concentration was 10 µg/mL: 15.84.

Results for the C0804 antibody in the case of using the siRNA against GPR87:
Geometric mean when the primary antibody was not added: 10.16; geometric mean when the primary antibody concentration was 0.1 µg/mL: 9.38; geometric mean when the primary antibody concentration was 1 µg/mL: 9.52; and geometric mean when the primary antibody concentration was 10 µg/mL: 10.18.

Results for the C0807 antibody in the case of using the control siRNA:
Geometric mean when the primary antibody was not added: 10.71; geometric mean when the primary antibody concentration was 0.1 µg/mL: 10.93; geometric mean when the primary antibody concentration was 1 µg/mL: 11.49; and geometric mean when the primary antibody concentration was 10 µg/mL: 16.35.

Results for the C0807 antibody in the case of using the siRNA against GPR87:
Geometric mean when the primary antibody was not added: 10.16; geometric mean when the primary antibody concentration was 0.1 µg/mL: 9.40; geometric mean when the primary antibody concentration was 1 µg/mL: 9.37; and geometric mean when the primary antibody concentration was 10 µg/mL: 10.35.

Results for the C0814 antibody in the case of using the control siRNA:
Geometric mean when the primary antibody was not added: 10.71; geometric mean when the primary antibody concentration was 0.1 µg/mL: 10.68; geometric mean when the primary antibody concentration was 1 µg/mL: 11.04; and geometric mean when the primary antibody concentration was 10 µg/mL: 12.27.

Results for the C0814 antibody in the case of using the siRNA against GPR87:
Geometric mean when the primary antibody was not added: 10.16; geometric mean when the primary antibody concentration was 0.1 µg/mL: 9.75; geometric mean when the primary antibody concentration was 1 µg/mL: 9.83; and geometric mean when the primary antibody concentration was 10 µg/mL: 9.94.

Results for the C0815 antibody in the case of using the control siRNA:
Geometric mean when the primary antibody was not added: 10.71; geometric mean when the primary antibody concentration was 0.1 µg/mL: 13.30; geometric mean when the primary antibody concentration was 1 µg/mL: 28.81; and geometric mean when the primary antibody concentration was 10 µg/mL: 60.52.

Results for the C0815 antibody in the case of using the siRNA against GPR87:
Geometric mean when the primary antibody was not added: 10.16; geometric mean when the primary antibody concentration was 0.1 µg/mL: 10.14; geometric mean when the primary antibody concentration was 1 µg/mL: 13.58; and geometric mean when the primary antibody concentration was 10 µg/mL: 22.39.

EXAMPLE 5

<Epitope Mapping>
In Example 5, epitope mapping by Western blotting was performed.

As mentioned above, GPR87 is a GPCR and four extracellular domains are present (see sequence Nos. 2 to 5). Fused proteins of polypeptides having the amino acid sequences of the respective extracellular domains and GST (glutathione S-transferase) were prepared and Western blotting was performed to examine the epitopes of the respective prepared antibodies.

DNAs encoding the amino acid sequences of the respective extracellular domains were synthesized and the DNAs were inserted in multicloning sites of GST fused protein expression vectors. *Escherichia coli* were transformed by the recombinant vectors and the Escherichia coli were cultured overnight in 5 mL cultures. The cultures were then diluted by 10 times, culturing in a 1 mL culture was performed for 2 hours, IPTG (isopropyl-β-D-thioglactopyranoside) was added to a final concentration of 0.5 mM, and culturing was performed for 2 hours to induce expression of the GST fused proteins.

The *Escherichia coli* that expressed the GST fused proteins were then collected by centrifugation, a sample buffer was added, SDS-PAGE was performed, and Western blotting was performed using the antibodies prepared in Example 2 as the primary antibodies.

The results are shown in FIG. 3.

In the figure, "lane M" indicates the result of Western blotting in the case of applying GST (control), "lane 1" indicates the result of Western blotting in the case of applying the fused protein of the polypeptide having the amino acid sequence of sequence No. 2 (the sequence of the 1st to 41st amino acids in full-length human GPR87) and GST, "lane 2" indicates the result of Western blotting in the case of applying the fused protein of the polypeptide having the amino acid sequence of sequence No. 3 (the sequence of the 101st to 118th amino acids in full-length human GPR87) and GST, "lane 3" indicates the result of Western blotting in the case of applying the fused protein of the polypeptide having the amino acid sequence of sequence No. 4 (the sequence of the 182nd to 206th amino acids in full-length human GPR87) and GST, and "lane 4" indicates the result of Western blotting in the case of applying the fused protein of the polypeptide having the amino acid sequence of sequence No. 5 (the sequence of the 280th to 298th amino acids in full-length human GPR87) and GST.

In the figure, "αGST" indicates that an anti-GST antibody was used as the primary antibody, "C0804" indicates that the C0804 antibody was used as the primary antibody, "C0812" indicates that the C0812 antibody was used as the primary antibody, "C0815" indicates that the C0815 antibody was used as the primary antibody, "C0806" indicates that the C0806 antibody was used as the primary antibody, "C0807" indicates that the C0807 antibody was used as the primary antibody, and "C0814" indicates that the C0814 antibody was used as the primary antibody.

As a result, a band was seen in lane 1 in each of the cases of using the C0804 antibody, C0812 antibody, C0815 antibody, C0806 antibody, C0807 antibody, and C0814 antibody as shown in FIG. 3.

The results indicate that the C0804 antibody, C0812 antibody, C0815 antibody, C0806 antibody, C0807 antibody, and C0814 antibody are respectively antibodies that recognize the extracellular domains of human GPR87 and that the epitope of each antibody is present at some position in the sequence of the 1st to 41st amino acids of full-length human GPR87.

EXAMPLE 6

<Epitope Mapping>

In Example 6, the epitope was examined by performing dot blotting using a synthetic polypeptide having the amino acid sequence of sequence No. 6 (15 amino acids).

As mentioned above, the amino acid sequence of sequence No. 6 is the portion included in the sequence of the extracellular domain closest to the N terminal side and is the sequence of the 9th to 24th amino acids of the full length.

The synthetic polypeptide was conjugated with KLH (keyhole limpet hemocyanin) and dropped onto a nitrocellulose membrane at various concentrations. Dot blotting was then performed using the antibodies prepared in Example 2 as the primary antibodies.

The results are shown in FIG. 4.

In the figure, "lane 1" indicates the result of dot blotting in the case of dropping the synthetic polypeptide having the amino acid sequence of sequence No. 6 and "lane 2" indicates the result of dot blotting in the case of dropping another synthetic polypeptide with 15 amino acids (control).

In the figure, "C0804" indicates that the C0804 antibody was used as the primary antibody, "C0812" indicates that the C0812 antibody was used as the primary antibody, "C0815" indicates that the C0815 antibody was used as the primary antibody, "C0806" indicates that the C0806 antibody was used as the primary antibody, "C0807" indicates that the C0807 antibody was used as the primary antibody, and "C0814" indicates that the C0814 antibody was used as the primary antibody.

In the figure, "1 µg," "0.1 µg," and "0.01 µg" indicate the dropping amounts of the synthetic peptide conjugated with KLH.

In the figure, "Ponceau S" indicates the results of staining the nitrocellulose membrane, onto which the synthetic polypeptide was dropped, with Ponceau S before performing dot blotting. "Dot blot" indicates the results of performing dot blotting.

As a result, a concentration-dependent dot was seen in lane 1 (lane on which the synthetic polypeptide having the amino acid sequence of sequence No. 6 was dropped) in each of the cases of using the C0804 antibody, C0812 antibody, C0815 antibody, C0806 antibody, C0807 antibody, and C0814 antibody as shown in FIG. 4.

The results indicate that the antibody epitope of each of the C0804 antibody, C0812 antibody, C0815 antibody, C0806 antibody, C0807 antibody, and C0814 antibody is present at some position in the sequence of the 9th to 23rd amino acids of full-length human GPR87.

EXAMPLE 7

<Immunohistological Staining>

In Example 7, immunostaining of cancerous tissue sections was attempted.

Paraffin sections of respective cancerous tissues were antigen-activated by autoclaving, adjusted to pH 6.5, and immunostained by a DAB immunostaining method. As the primary antibody, the C0804 antibody was used upon adjusting to a concentration of 40 µg/mL.

The result of immunostaining of lung squamous cell carcinoma is shown in FIG. 5.

As shown in FIG. 5, by use of the antibody according to the present invention, a strongly positively stained image was observed with the tissue section of lung squamous cell carcinoma.

Besides the above, strongly positively stained images were observed with prickle cell carcinoma (squamous cell carcinoma) of skin, tongue cancer (squamous cell carcinoma), squamous cell carcinoma of the pharynx, malignant lymphoma of the pharynx, squamous cell carcinoma of the larynx, and squamous cell carcinoma of the bladder, positively stained images were observed with basal cell carcinoma of skin, melanoma of skin, small cell carcinoma of the lung, squamous cell carcinoma of the esophagus, adenocarcinoma of the esophagus, tubular adenocarcinoma of the pancreas, cervical cancer (squamous cell carcinoma), transitional cell carcinoma of the bladder, renal pelvis or ureter cancer (transitional cell carcinoma), uterine cancer (adenocarcinoma), and breast cancer (adenocarcinoma), and weakly positively stained images were observed with adenocarcinoma of the lung, stomach cancer (adenocarcinoma), and colon cancer (adenocarcinoma).

EXAMPLE 8

<ADCC Activity>

In Example 8, ADCC activities of the respective purified antibodies obtained in Example 2 were examined.

$2\times10^6$ target cells were suspended in 200 µL, of a culture medium, 16 µL, of $^{51}$Cr(185 MBq/mL; purchased from PerkinElmer Inc.) were added, incubation under 37° C. was performed for 1.5 hours to make the $^{51}$Cr be taken up into the cells, and thereafter, $1\times10^4$ (50µL) of the cells were placed in each well of a 96-well plate. As the target cells, the stable expression cell line established in Example 1 was used, and the wild cell line of CHO cells was used as a comparative example.

Each of the six types of antibodies obtained in Example 2 were adjusted to final concentrations of 0.001, 0.01, 0.1, 1, and 10 µg/mL and 50 µL of each were added to each well. The same amount of culture medium was added in place of the antibody as a control.

$1\times10^5$ (100 µL) effector cells were then added. Incubation under 37° C. was then performed for 4 hours. As the effector cells, bone marrow cells collected from a mouse and cultured for 6 days on a culture medium with GM-CSF (final concentration: 10 ng/mL) and IL-2 (final concentration: 50 ng/mL) added were used.

When target cells are destroyed by the ADCC activity, $^{51}$Cr is released into the culture supernatant. Thus, after incubation, the culture supernatants of the respective wells were recovered and measured with a gamma counter.

At the same time, to determine the value of the amount of $^{51}$Cr taken into the cells, $1\times10^4$ target cells were made to take up $^{51}$Cr, 2% NP-40 was thereafter added to destroy all target cells, and then the culture supernatant was recovered and measured with the gamma counter.

The gamma counter measurement value in the case of adding the same amount of medium in place of the antibody was then subtracted from the respective measurement values in the cases of adding the respective antibodies (A), the measurement value in the case of adding the same amount of medium in place of the antibody was subtracted from the measurement value of the amount of $^{51}$Cr taken into the cells (B), and then the values obtained by dividing the respective values of (A) by the value of (B) were multiplied by 100 to determine the ADCC activity values (%).

The results are shown in FIG. 6. FIG. 6 is a graph of the ADCC activity measurement results. In the graph, the abscissa indicates the antibody concentration (μg/mL) and the ordinate indicates the ADCC activity (%). "Stable CHO" (solid broken line) indicates the ADCC activity in the case of using the stable expression cell line established in Example 1 as the target cells, "wild CHO" (dotted broken line) indicates the ADCC activity in the case of using the wild line of CHO cells as the target cells, "C0804," "C0812," "C0815," "C0806," "C0807," and "C0814" indicate the ADCC activities in the cases of adding the respective antibodies.

As shown in FIG. 6, with all of the antibodies, the ADCC activity values in the case of using the stable expression cell line established in Example 1 were higher than those in the case of using the wild line of CHO cells. All of the respective purified antibodies obtained in Example 2 were thus found to have ADCC activity.

EXAMPLE 9

<PET>

In Example 9, whether or not an antibody according to the present invention accumulates in cancerous tissue even in vivo was examined using microPET.

An antibody according to the present invention was modified with a radioisotope and administered to a tumor-bearing model mouse and the radiation was detected and image with a microPET apparatus.

$1\times10^7$ ME180 cells were subcutaneously implanted in a right shoulder portion of a nude mouse (Balb/c, 5 weeks old, female) and the mouse was reared for 4 weeks to prepare the tumor-bearing model mouse. The size of the tumor 4 weeks after implantation was approximately 1.000 mm$^3$.

The above-described C0804 antibody and S-2-(4-isothiocyanatobenzyl)-1,4,7,10-tetraazacyclododecane-tetraacetic acid (made by Macrocyclics Inc., hereinafter referred to as "DOTA") were mixed at (a molar ratio of) 1:10 and the mixture was left still under room temperature for 24 hours to form a DOTA-antibody conjugate. $^{64}$Cu was then coordination-bonded to the DOTA portion of the antibody to thereby modify the antibody with the radioisotope. After the modification, the antibody concentration was 405.0 μg/mL and the radiation concentration was 43.1 MBq/mL.

The prepared tumor-bearing mouse was administered with 5 MBq of the radioisotope modified antibody and then imaged by microPET 72 hours later. With the mouse under isoflurane anesthesia, imaging (emission scan) was performed for 180 minutes from the point of 72 hours after antibody administration using "Inveon PET (made by Siemens AG)," and the collected data were reconstituted by a 3D-MAP method (OSEM 3D/MAP; 3D-ordered subset-expectation maximization/maximum a priori).

The results are shown in FIG. 7. FIG. 7 shows PET imaging data upon administration of the radioisotope modified antibody to the tumor-bearing model mouse. The data are reconstituted to a state of viewing the mouse from the back side (upper side) and in the figure, the upper side is the front (head side) and the lower side is the rear (tail portion side).

As shown in FIG. 7, as a result of administering the radioisotope modified antibody to the tumor-bearing mouse, specific accumulation of the radioisotope modified antibody was detected at the cancerous portion (right shoulder portion, see arrow in the figure).

This result indicates that the antibody according to the present invention accumulates specifically in cancerous tissue even in vivo, in other words, is effective for diagnosis and treatment of various tumors in which GPR87 is highly expressed.

EXAMPLE 10

<CDR Analysis>

In Example 10, the amino acid sequences of the CDRs of the respective purified antibodies obtained in Example 2 were determined.

From the hybridoma established in Example 2, total RNA was extracted using "RNeasy Plus Mini Kit" (made by Qiagen) and then converted to cDNA, and thereafter PCR was performed using "Mouse Ig-Primer Set" (made by Novagen) to amplify DNAs encoding vicinities of the N terminals of the H chain and L chain of the respective antibodies.

The amplified DNAs were then gel purified, inserted in a T-vector, and the sequences thereof were measured.

The base sequence obtained from the H chain of the C0804 antibody is shown in sequence No. 8, the base sequence obtained from the L chain of the C0804 antibody is shown in sequence No. 9, the base sequence obtained from the H chain of the C0812 antibody is shown in sequence No. 10, the base sequence obtained from the L chain of the C0812 antibody is shown in sequence No. 11, the base sequence obtained from the H chain of the C0815 antibody is shown in sequence No. 12, and the base sequence obtained from the L chain of the C0815 antibody is shown in sequence No. 13. These sequences are partial-length sequences at the 5' terminal side that begin with a start codon.

The partial-length amino acid sequence from the N terminal of the H chain of the C0804 antibody translated based on the above sequence information is shown in sequence No. 14, the partial-length amino acid sequence from the N terminal of the L chain of the C0804 antibody is shown in sequence No. 15, the partial-length amino acid sequence from the N terminal of the H chain of the C0812 antibody is shown in sequence No. 16, the partial-length amino acid sequence from the N terminal of the L chain of the C0812 antibody is shown in sequence No. 17, the partial-length amino acid sequence from the N terminal of the H chain of the C0815 antibody is shown in sequence No. 18, and the partial-length amino acid sequence from the N terminal of the L chain of the C0815 antibody is shown in sequence No. 19.

For the H chain of the C0804 antibody, the amino acid sequence of CDR1 inferred from the above sequence information is shown in sequence No. 20, the amino acid sequence of CDR2 is shown in sequence No. 21, and the amino acid sequence of CDR3 is shown in sequence No. 22.

Likewise, for the L chain of the C0804 antibody, the amino acid sequence of CDR1 is shown in sequence No. 23, the amino acid sequence of CDR2 is shown in sequence No. 24, and the amino acid sequence of CDR3 is shown in sequence No. 25.

Likewise, for the H chain of the C0812 antibody, the amino acid sequence of CDR1 is shown in sequence No. 26, the amino acid sequence of CDR2 is shown in sequence No. 27, and the amino acid sequence of CDR3 is shown in sequence No. 28. Likewise, for the L chain of the C0812 antibody, the amino acid sequence of CDR1 is shown in sequence No. 29, the amino acid sequence of CDR2 is shown in sequence No. 30, and the amino acid sequence of CDR3 is shown in sequence No. 31.

Likewise, for the H chain of the C0815 antibody, the amino acid sequence of CDR1 is shown in sequence No. 32, the amino acid sequence of CDR2 is shown in sequence No. 33, and the amino acid sequence of CDR3 is shown in sequence No. 34. Likewise, for the L chain of the C0815 antibody, the amino acid sequence of CDR1 is shown in sequence No. 35, the amino acid sequence of CDR2 is shown in sequence No. 36, and the amino acid sequence of CDR3 is shown in sequence No. 37.

Industrial Applicability

The antibodies according to the present invention are useful in biochemical analysis of GPR87 and immunohistological diagnosis, etc., of tumors, and also potentially useful in PET diagnosis, antibodies for treatment, etc., of tumors.

---

SEQUENCE LISTING

<160> NUMBER OF SEQ ID NOS: 37

Figure 1A:
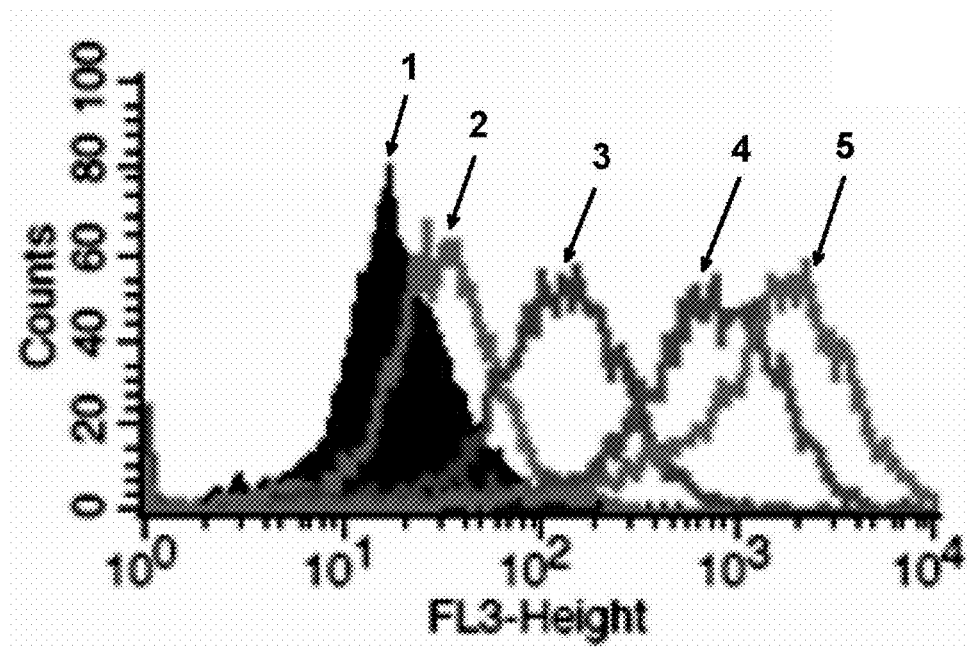
[FIG. 1A] is a diagram of results of performing flow cytometry in Example 3 using a human GPR87 stable expression cell line established in Example 1 as cells and using a C0804 antibody as a primary antibody.
Figure 1B:
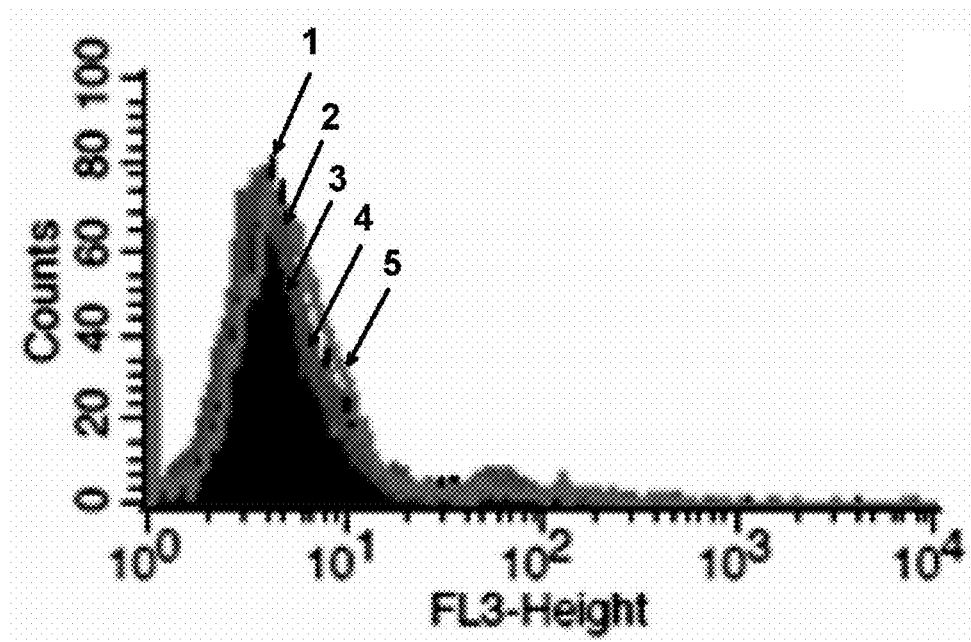
[FIG. 1B] is a diagram of results of performing flow cytometry in Example 3 using a wild line of CHO cells as the cells and using the C0804 antibody as the primary antibody (control).
Figure 2A:
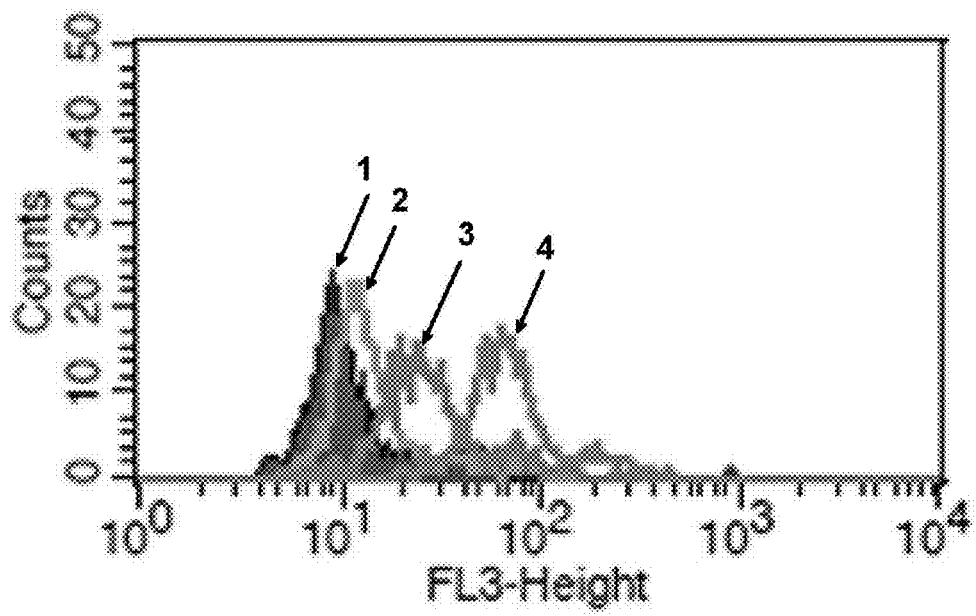
[FIG. 2A] is a diagram of results of performing flow cytometry in Example 4 using Me180 cells transfected with a control siRNA as the cells and using the C0804 antibody as the primary antibody (control).
Figure 2B:
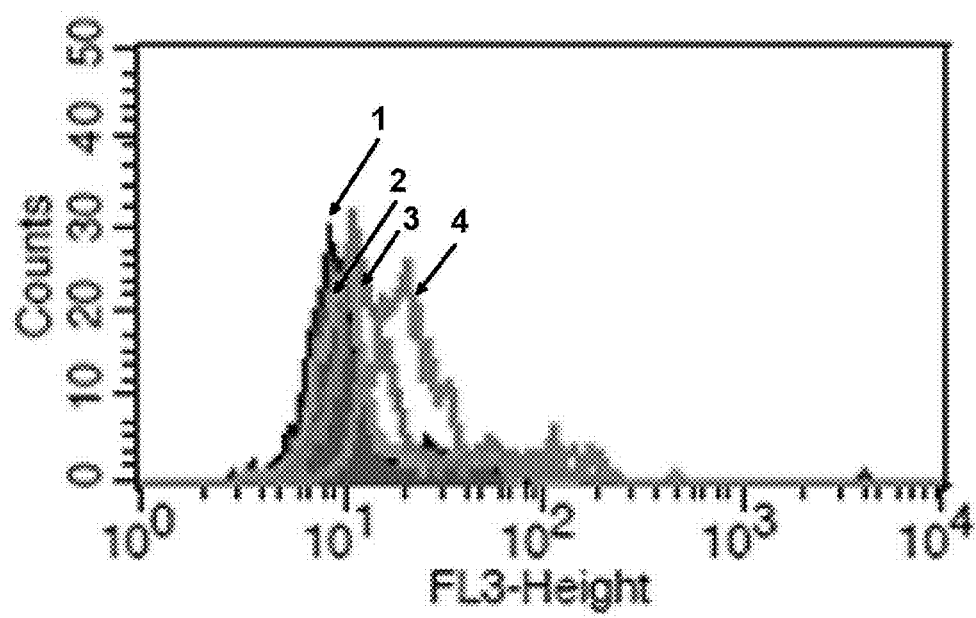
[FIG. 2B] is a diagram of results of performing flow cytometry in Example 4 using Me180 cells transfected with siRNA against human GPR87 as the cells and using the C0804 antibody as the primary antibody.
Figure 3:
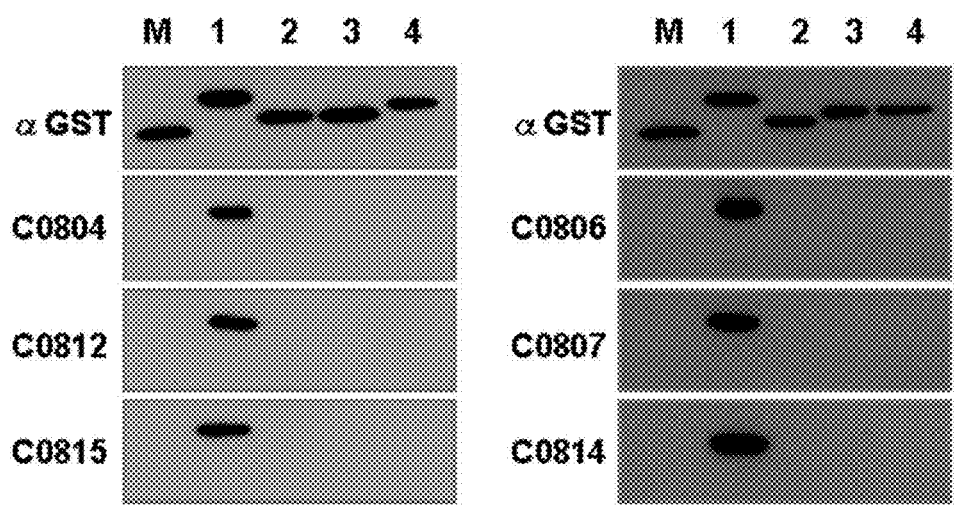
[FIG. 3] is a photograph of results of performing Western blotting in Example 5.
Figure 4:
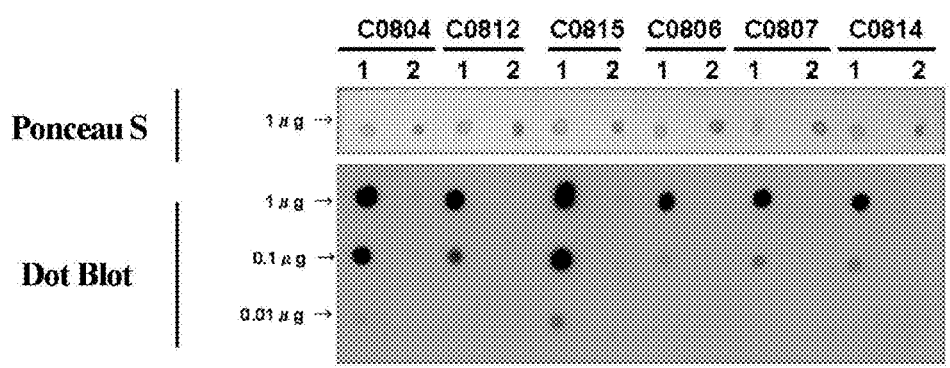
[FIG. 4] is a photograph of results of performing dot blotting in Example 6.
Figure 5:
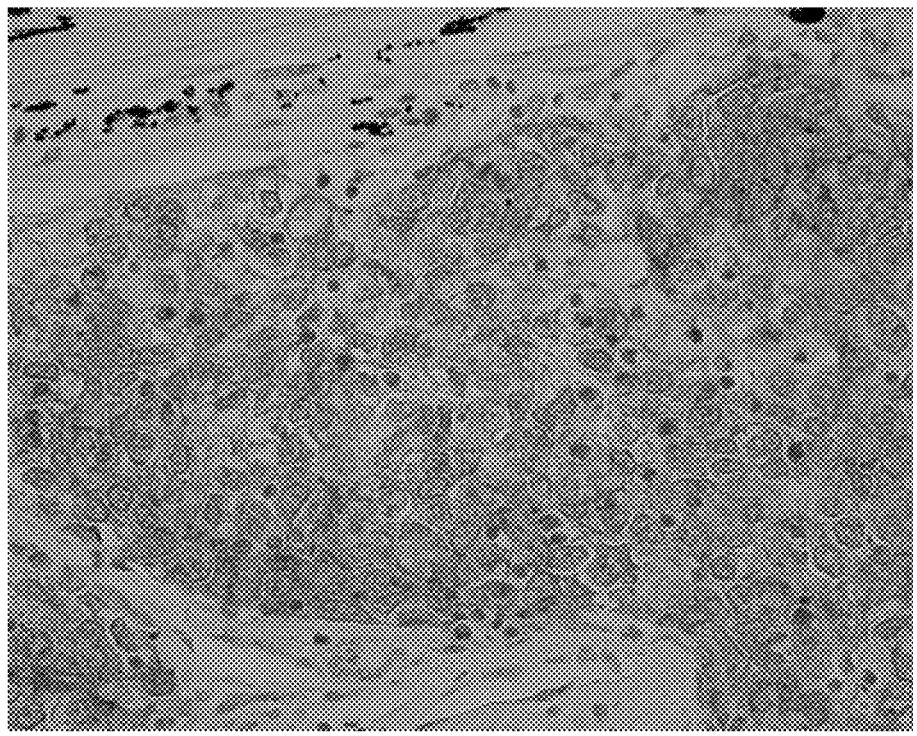
[FIG. 5] is a photograph of results of immunohistological staining of lung squamous cell carcinoma in Example 7.
Figure 6:
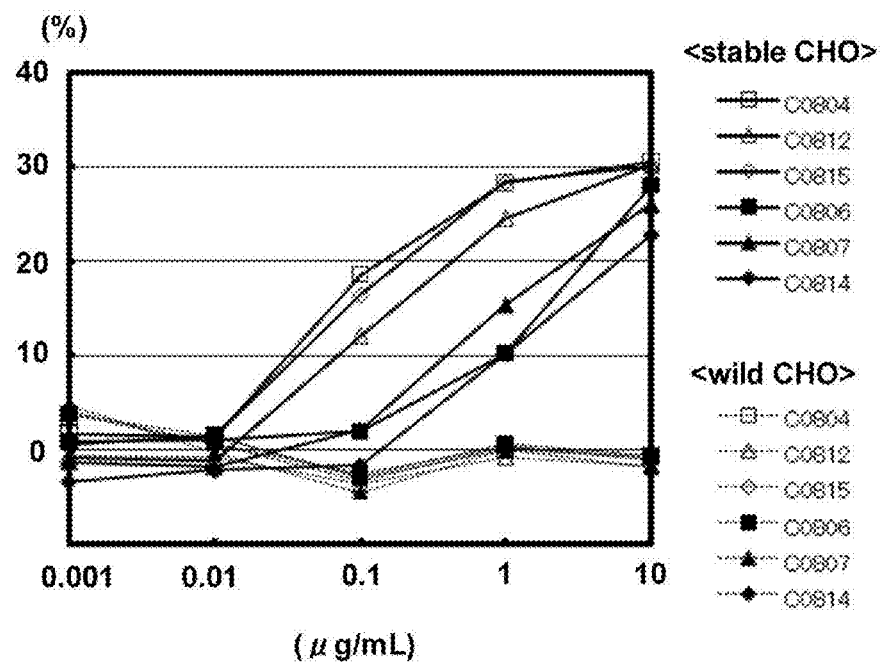
[FIG. 6] is a graph of ADCC activity measurement results in Example 8.
Figure 7:
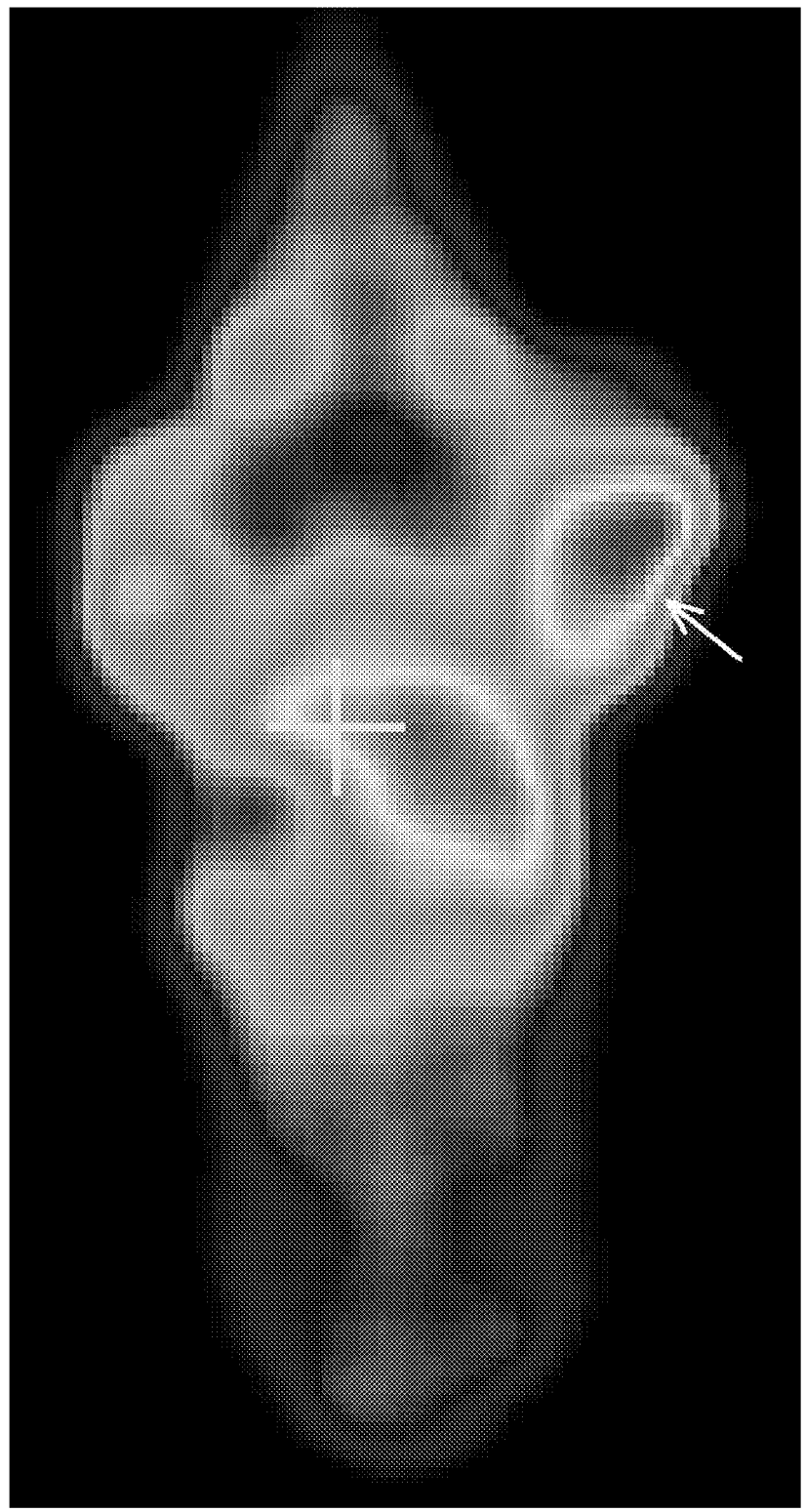
[FIG. 7] shows PET imaging data obtained upon administering a radioisotope modified antibody to a tumor-bearing model mouse in Example 9.

<210> SEQ ID NO 1
<211> LENGTH: 358
<212> TYPE: PRT
<213> ORGANISM: Homo sapiens

<400> SEQUENCE: 1

```
Met Gly Phe Asn Leu Thr Leu Ala Lys Leu Pro Asn Asn Glu Leu His
1               5                   10                  15

Gly Gln Glu Ser His Asn Ser Gly Asn Arg Ser Asp Gly Pro Gly Lys
            20                  25                  30

Asn Thr Thr Leu His Asn Glu Phe Asp Thr Ile Val Leu Pro Val Leu
        35                  40                  45

Tyr Leu Ile Ile Phe Val Ala Ser Ile Leu Leu Asn Gly Leu Ala Val
    50                  55                  60

Trp Ile Phe Phe His Ile Arg Asn Lys Thr Ser Phe Ile Phe Tyr Leu
65                  70                  75                  80

Lys Asn Ile Val Val Ala Asp Leu Ile Met Thr Leu Thr Phe Pro Phe
                85                  90                  95

Arg Ile Val His Asp Ala Gly Phe Gly Pro Trp Tyr Phe Lys Phe Ile
            100                 105                 110

Leu Cys Arg Tyr Thr Ser Val Leu Phe Tyr Ala Asn Met Tyr Thr Ser
        115                 120                 125

Ile Val Phe Leu Gly Leu Ile Ser Ile Asp Arg Tyr Leu Lys Val Val
    130                 135                 140

Lys Pro Phe Gly Asp Ser Arg Met Tyr Asn Ile Thr Phe Thr Lys Val
145                 150                 155                 160

Leu Ser Val Cys Val Trp Val Ile Met Ala Val Leu Ser Leu Pro Asn
                165                 170                 175

Ile Ile Leu Thr Asn Gly Gln Pro Thr Glu Asp Asn Ile His Asp Cys
            180                 185                 190

Ser Lys Leu Lys Ser Pro Leu Gly Val Lys Trp His Thr Ala Val Thr
        195                 200                 205

Tyr Val Asn Ser Cys Leu Phe Val Ala Val Leu Val Ile Leu Ile Gly
    210                 215                 220

Cys Tyr Ile Ala Ile Ser Arg Tyr Ile His Lys Ser Ser Arg Gln Phe
```

```
                225                 230                 235                 240
Ile Ser Gln Ser Ser Arg Lys Arg Lys His Asn Gln Ser Ile Arg Val
                    245                 250                 255

Val Val Ala Val Phe Phe Thr Cys Phe Leu Pro Tyr His Leu Cys Arg
                260                 265                 270

Ile Pro Phe Thr Phe Ser His Leu Asp Arg Leu Leu Asp Glu Ser Ala
            275                 280                 285

Gln Lys Ile Leu Tyr Tyr Cys Lys Glu Ile Thr Leu Phe Leu Ser Ala
        290                 295                 300

Cys Asn Val Cys Leu Asp Pro Ile Ile Tyr Phe Phe Met Cys Arg Ser
305                 310                 315                 320

Phe Ser Arg Arg Leu Phe Lys Lys Ser Asn Ile Arg Thr Arg Ser Glu
                325                 330                 335

Ser Ile Arg Ser Leu Gln Ser Val Arg Arg Ser Glu Val Arg Ile Tyr
            340                 345                 350

Tyr Asp Tyr Thr Asp Val
        355

<210> SEQ ID NO 2
<211> LENGTH: 41
<212> TYPE: PRT
<213> ORGANISM: artificial sequence
<220> FEATURE:
<223> OTHER INFORMATION: 1st extracellular region of hGPR87

<400> SEQUENCE: 2

Met Gly Phe Asn Leu Thr Leu Ala Lys Leu Pro Asn Asn Glu Leu His
1               5                   10                  15

Gly Gln Glu Ser His Asn Ser Gly Asn Arg Ser Asp Gly Pro Gly Lys
            20                  25                  30

Asn Thr Thr Leu His Asn Glu Phe Asp
        35                  40

<210> SEQ ID NO 3
<211> LENGTH: 18
<212> TYPE: PRT
<213> ORGANISM: artificial sequence
<220> FEATURE:
<223> OTHER INFORMATION: 2nd extracellular region of hGPR87

<400> SEQUENCE: 3

His Asp Ala Gly Phe Gly Pro Trp Tyr Phe Lys Phe Ile Leu Cys Arg
1               5                   10                  15

Tyr Thr

<210> SEQ ID NO 4
<211> LENGTH: 25
<212> TYPE: PRT
<213> ORGANISM: artificial sequence
<220> FEATURE:
<223> OTHER INFORMATION: 3rd extracellular region of hGPR87

<400> SEQUENCE: 4

Asn Gly Gln Pro Thr Glu Asp Asn Ile His Asp Cys Ser Lys Leu Lys
1               5                   10                  15

Ser Pro Leu Gly Val Lys Trp His Thr
            20                  25

<210> SEQ ID NO 5
<211> LENGTH: 19
```

```
<212> TYPE: PRT
<213> ORGANISM: artificial sequence
<220> FEATURE:
<223> OTHER INFORMATION: 4th extracellular region of hGPR87

<400> SEQUENCE: 5

His Leu Asp Arg Leu Leu Asp Glu Ser Ala Gln Lys Ile Leu Tyr Tyr
1               5                   10                  15

Cys Lys Glu

<210> SEQ ID NO 6
<211> LENGTH: 15
<212> TYPE: PRT
<213> ORGANISM: artificial sequence
<220> FEATURE:
<223> OTHER INFORMATION: epitope of antibody in 1st extracellular region
      of hGPR87

<400> SEQUENCE: 6

Lys Leu Pro Asn Asn Glu Leu His Gly Gln Glu Ser His Asn Ser
1               5                   10                  15

<210> SEQ ID NO 7
<211> LENGTH: 25
<212> TYPE: RNA
<213> ORGANISM: artificial sequence
<220> FEATURE:
<223> OTHER INFORMATION: siRNA against hGPR87

<400> SEQUENCE: 7
aauauaugcg aacuuccgau cuucu                                         25

<210> SEQ ID NO 8
<211> LENGTH: 443
<212> TYPE: DNA
<213> ORGANISM: artificial sequence
<220> FEATURE:
<223> OTHER INFORMATION: partial CDS of heavy chain of C0804 antibody

<400> SEQUENCE: 8
atggcttggg tgtggacctt gctattcctg atggcagctg cccaaagtat ccaagcacag    60
atccagttgg tgcagtctgg acctgagctg aagaagcctg agagacagt caagatctcc    120 tgcaaggtct ctggttatac cttcacagac tattcaatgc actgggtgaa gcaggctcca   180
ggaaagggtt taaagtggat ggcctggata aacactgaga ctggtaaacc aacatatgca   240
gatgacttca agggacggtt tgccttctct ttggaagcct ctgccagcac tgcctatttg   300
cagatcaaca acctcaaaaa tgaggacacg gctacatatt tctgtgcctc actcgactac   360
tgggcccaag gcaccactct cacagtttct tcagccaaaa cgacaccccc accgtctat    420 cccctggccc ctggaagctt ggg                                          443

<210> SEQ ID NO 9
<211> LENGTH: 447
<212> TYPE: DNA
<213> ORGANISM: artificial sequence
<220> FEATURE:
<223> OTHER INFORMATION: partial CDS of light chain of C0804 antibody

<400> SEQUENCE: 9
atgaagttgc tgttaggct gttggtgctg atgttctgga ttcctgcttc caacagtgat    60
gttttgatga cccaaactcc actctccctg cctgtcagtc ttggagatca agcctccatc   120
tcttgcagat ctagtcagaa cgttgtacat agtagtggaa acacctattt agaatggttc   180
```

```
ctgcagaaac caggccagtc tccaaagctc ctgatctaca agtttccac ccgattttct       240 ggggtcccag acaggttcag tggcagtgga tcagggacag atttcacact caagatcagc       300
agagtggagg ctgaggatct ggagtttat tactgctttc aaggttcaca tgttccgtac        360
acgttcggag gggggaccaa gctggaaata aaacgggctg atgctgcacc aactgtatcc       420
atcttcccac catccagtaa gcttggg                                           447

<210> SEQ ID NO 10
<211> LENGTH: 443
<212> TYPE: DNA
<213> ORGANISM: artificial sequence
<220> FEATURE:
<223> OTHER INFORMATION: partial CDS of heavy chain of C0812 antibody

<400> SEQUENCE: 10
atggaatgga gctgggtctt cctcttcctc ctgtcaggaa ctgcaggtgt ccactctgag       60
gtccagctgc aacagtctgg acctgacctg gtgaagcctg agcttcaat gaagatatcc       120 tgcaaggctt ctggttactc attcactgac tacaccatgc actgggtgaa gcagagccat       180
ggaaagaact tgagtggat tggacttatt aatccttaca atgatggtac tacctacaac       240
cagaagttca agggcaaggc cacattaact gtagacaagt catctagcac agcctacatg       300
gagctcctca gtctgacatc tgaggactct gcagtctatt actgtgcatc attggactac       360
tggggtcaag gaacctcagt caccgtctcc tcagccaaaa cgacaccccc accgtttat       420 cccctggccc ctggaagctt ggg                                               443

<210> SEQ ID NO 11
<211> LENGTH: 447
<212> TYPE: DNA
<213> ORGANISM: artificial sequence
<220> FEATURE:
<223> OTHER INFORMATION: partial CDS of light chain of C0812 antibody

<400> SEQUENCE: 11
atgaagttgc ctgttaggct gttggtgctg atgttctgga ttcctgcttc cagcagtgat       60
gttgtgatga cccaaactcc actctccctg cctgtcagtc ttggagatca agcctccatc       120
tcttgcagat ctagtcagag ccttgtacac agtagtggaa acacctattt acattggtac       180
ctgcagaagc caggccagtc tccaaagctc ctgatctaca agtttccaa ccgattttct        240 ggggtcccgg acaggttcag tggcagtgga tcagggacag atttcacact caagatcagc      300
agagtggagg ctgaggatct ggagtttat ttctgctctc aaagtacgca tgttccgtac        360
acgttcggag gggggaccaa gctggaaata aaacgggctg atgctgcacc aactgtatcc      420
atcttcccac catccagtaa gcttggg                                           447

<210> SEQ ID NO 12
<211> LENGTH: 443
<212> TYPE: DNA
<213> ORGANISM: artificial sequence
<220> FEATURE:
<223> OTHER INFORMATION: partial CDS of heavy chain of C0815 antibody

<400> SEQUENCE: 12
atggcttggg tgtggacctt gctattcctg atggcagctg cccaaagtat ccaagcacag       60
atccagttgg tgcagtctgg acctgagctg aagaaccctg agagacagt caagatctcc        120 tgcaaggtct ctggttatac cttcacagac tattcaatgc actgggtgaa gcaggctcca      180
```

```
ggaaagggtt taaagtggat ggcctggata aacactgaga ctggtaaacc aacatatgca    240
gatgacttca agggacggtt tgccttctct ttggaaacct ctgccagcac tgcctatttg    300
cagatcaaca ccctcaaaaa tgaggacacg gctacatatt tctgtgcctc actcgactac    360
tggggccaag gcaccactct cacagtttct tcagccaaaa cgacaccccc atccgtctat    420
ccactggccc ctggaagctt ggg                                            443

<210> SEQ ID NO 13
<211> LENGTH: 447
<212> TYPE: DNA
<213> ORGANISM: artificial sequence
<220> FEATURE:
<223> OTHER INFORMATION: partial CDS of light chain of C0815 antibody

<400> SEQUENCE: 13
atgaagttgc ctgttaggct gttggtgctg atgttctgga ttcctgcttc cagcagtgat     60
gttttgatga cccaaactcc actctccctg cctgtcagtc ttggagatca agcctccatc    120
tcttgcagat ctagtcagaa cgttgtacat agtagtggaa acacctattt agaatggttc    180
ctgcagaaac caggccagtc tccaaagctc ctgatctaca agtttccaa ccgattttct    240 ggggtcccag acaggttcag tggcagtgga tcagggacaa tttcacact caagatcagc    300 agagtggagg ctgaggatct gggagtttat tactgctttc aaggttcaca tgttccgtac    360
acgttcggag ggggaccaa gctggaaata aaacgggctg atgctgcacc aactgtatcc    420
atcttcccac catccagtaa gcttggg                                       447

<210> SEQ ID NO 14
<211> LENGTH: 147
<212> TYPE: PRT
<213> ORGANISM: artificial sequence
<220> FEATURE:
<223> OTHER INFORMATION: partial sequence of amino acid of heavy chain
      of C0804 antibody

<400> SEQUENCE: 14

Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Val Ser Gly Tyr Thr Phe
        35                  40                  45

Thr Asp Tyr Ser Met His Trp Val Lys Gln Ala Pro Gly Lys Gly Leu
    50                  55                  60

Lys Trp Met Ala Trp Ile Asn Thr Glu Thr Gly Lys Pro Thr Tyr Ala
65                  70                  75                  80

Asp Asp Phe Lys Gly Arg Phe Ala Phe Ser Leu Glu Ala Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Ser Leu Asp Tyr Trp Gly Gln Gly Thr Thr Leu Thr
        115                 120                 125

Val Ser Ser Ala Lys Thr Thr Pro Pro Val Tyr Pro Leu Ala Pro
    130                 135                 140

Gly Ser Leu
145

<210> SEQ ID NO 15
```

```
<211> LENGTH: 149
<212> TYPE: PRT
<213> ORGANISM: artificial sequence
<220> FEATURE:
<223> OTHER INFORMATION: partial sequence of amino acid of light chain
      of C0804 antibody

<400> SEQUENCE: 15

Met Lys Leu Pro Val Arg Leu Leu Val Leu Met Phe Trp Ile Pro Ala
1               5                   10                  15

Ser Asn Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Asn Val
        35                  40                  45

Val His Ser Ser Gly Asn Thr Tyr Leu Glu Trp Phe Leu Gln Lys Pro
    50                  55                  60

Gly Gln Ser Pro Lys Leu Leu Ile Tyr Lys Val Ser Thr Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Tyr Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Lys Leu Gly
145

<210> SEQ ID NO 16
<211> LENGTH: 147
<212> TYPE: PRT
<213> ORGANISM: artificial sequence
<220> FEATURE:
<223> OTHER INFORMATION: partial sequence of amino acid of heavy chain
      of C0812 antibody

<400> SEQUENCE: 16

Met Glu Trp Ser Trp Val Phe Leu Phe Leu Leu Ser Gly Thr Ala Gly
1               5                   10                  15

Val His Ser Glu Val Gln Leu Gln Gln Ser Gly Pro Asp Leu Val Lys
            20                  25                  30

Pro Gly Ala Ser Met Lys Ile Ser Cys Lys Ala Ser Gly Tyr Ser Phe
        35                  40                  45

Thr Asp Tyr Thr Met His Trp Val Lys Gln Ser His Gly Lys Asn Phe
    50                  55                  60

Glu Trp Ile Gly Leu Ile Asn Pro Tyr Asn Asp Gly Thr Thr Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Ser Leu Asp Tyr Trp Gly Gln Gly Thr Ser Val Thr
        115                 120                 125

Val Ser Ser Ala Lys Thr Thr Pro Pro Val Tyr Pro Leu Ala Pro
    130                 135                 140

Gly Ser Leu
145
```

```
<210> SEQ ID NO 17
<211> LENGTH: 149
<212> TYPE: PRT
<213> ORGANISM: artificial sequence
<220> FEATURE:
<223> OTHER INFORMATION: partial sequence of amino acid of light chain
      of C0812 antibody

<400> SEQUENCE: 17

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Gln Ser Leu
        35                  40                  45

Val His Ser Ser Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Tyr Thr Phe Gly Gly Gly Thr Lys Leu
        115                 120                 125

Glu Ile Lys Arg Ala Asp Ala Ala Pro Thr Val Ser Ile Phe Pro Pro
130                 135                 140

Ser Ser Lys Leu Gly
145

<210> SEQ ID NO 18
<211> LENGTH: 147
<212> TYPE: PRT
<213> ORGANISM: artificial sequence
<220> FEATURE:
<223> OTHER INFORMATION: partial sequence of amino acid of heavy chain
      of C0815 antibody

<400> SEQUENCE: 18

Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Asn
            20                  25                  30

Pro Gly Glu Thr Val Lys Ile Ser Cys Lys Val Ser Gly Tyr Thr Phe
        35                  40                  45

Thr Asp Tyr Ser Met His Trp Val Lys Gln Ala Pro Gly Lys Gly Leu
    50                  55                  60

Lys Trp Met Ala Trp Ile Asn Thr Glu Thr Gly Lys Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Thr Leu Lys Asn Glu Asp Thr Ala Thr
            100                 105                 110

Tyr Phe Cys Ala Ser Leu Asp Tyr Trp Gly Gln Gly Thr Thr Leu Thr
        115                 120                 125

Val Ser Ser Ala Lys Thr Thr Pro Pro Ser Val Tyr Pro Leu Ala Pro
    130                 135                 140
```

```
Gly Ser Leu
145

<210> SEQ ID NO 19
<211> LENGTH: 149
<212> TYPE: PRT
<213> ORGANISM: artificial sequence
<220> FEATURE:
<223> OTHER INFORMATION: partial sequence of amino acid of light chain
      of C0815 antibody

<400> SEQUENCE: 19

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Asn Val
        35                  40                  45

Val His Ser Ser Gly Asn Thr Tyr Leu Glu Trp Phe Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Tyr Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Lys Leu Gly
145

<210> SEQ ID NO 20
<211> LENGTH: 5
<212> TYPE: PRT
<213> ORGANISM: artificial sequence
<220> FEATURE:
<223> OTHER INFORMATION: CDR1 of heavy chain of C0804 antibody

<400> SEQUENCE: 20

Asp Tyr Ser Met His
1               5

<210> SEQ ID NO 21
<211> LENGTH: 17
<212> TYPE: PRT
<213> ORGANISM: artificial sequence
<220> FEATURE:
<223> OTHER INFORMATION: CDR2 of heavy chain of C0804 antibody

<400> SEQUENCE: 21

Trp Ile Asn Thr Glu Thr Gly Lys Pro Thr Tyr Ala Asp Asp Phe Lys
1               5                   10                  15

Gly

<210> SEQ ID NO 22
<211> LENGTH: 3
<212> TYPE: PRT
<213> ORGANISM: artificial sequence
<220> FEATURE:
```

```
<223> OTHER INFORMATION: CDR3 of heavy chain of C0804 antibody

<400> SEQUENCE: 22

Leu Asp Tyr
1

<210> SEQ ID NO 23
<211> LENGTH: 16
<212> TYPE: PRT
<213> ORGANISM: artificial sequence
<220> FEATURE:
<223> OTHER INFORMATION: CDR1 of light chain of C0804 antibody

<400> SEQUENCE: 23

Arg Ser Ser Gln Asn Val Val His Ser Ser Gly Asn Thr Tyr Leu Glu
1               5                   10                  15

<210> SEQ ID NO 24
<211> LENGTH: 7
<212> TYPE: PRT
<213> ORGANISM: artificial sequence
<220> FEATURE:
<223> OTHER INFORMATION: CDR2 of light chain of C0804 antibody

<400> SEQUENCE: 24

Lys Val Ser Thr Arg Phe Ser
1               5

<210> SEQ ID NO 25
<211> LENGTH: 9
<212> TYPE: PRT
<213> ORGANISM: artificial sequence
<220> FEATURE:
<223> OTHER INFORMATION: CDR3 of light chain of C0804 antibody

<400> SEQUENCE: 25

Phe Gln Gly Ser His Val Pro Tyr Thr
1               5

<210> SEQ ID NO 26
<211> LENGTH: 5
<212> TYPE: PRT
<213> ORGANISM: artificial sequence
<220> FEATURE:
<223> OTHER INFORMATION: CDR1 of heavy chain of C0812 antibody

<400> SEQUENCE: 26

Asp Tyr Thr Met His
1               5

<210> SEQ ID NO 27
<211> LENGTH: 17
<212> TYPE: PRT
<213> ORGANISM: artificial sequence
<220> FEATURE:
<223> OTHER INFORMATION: CDR2 of heavy chain of C0812 antibody

<400> SEQUENCE: 27

Leu Ile Asn Pro Tyr Asn Asp Gly Thr Thr Tyr Asn Gln Lys Phe Lys
1               5                   10                  15

Gly

<210> SEQ ID NO 28
<211> LENGTH: 3
<212> TYPE: PRT
<213> ORGANISM: artificial sequence
```

```
<220> FEATURE:
<223> OTHER INFORMATION: CDR3 of heavy chain of C0812 antibody

<400> SEQUENCE: 28

Leu Asp Tyr
1

<210> SEQ ID NO 29
<211> LENGTH: 16
<212> TYPE: PRT
<213> ORGANISM: artificial sequence
<220> FEATURE:
<223> OTHER INFORMATION: CDR1 of light chain of C0812 antibody

<400> SEQUENCE: 29

Arg Ser Ser Gln Ser Leu Val His Ser Ser Gly Asn Thr Tyr Leu His
1               5                   10                  15

<210> SEQ ID NO 30
<211> LENGTH: 7
<212> TYPE: PRT
<213> ORGANISM: artificial sequence
<220> FEATURE:
<223> OTHER INFORMATION: CDR2 of light chain of C0812 antibody

<400> SEQUENCE: 30

Lys Val Ser Asn Arg Phe Ser
1               5

<210> SEQ ID NO 31
<211> LENGTH: 9
<212> TYPE: PRT
<213> ORGANISM: artificial sequence
<220> FEATURE:
<223> OTHER INFORMATION: CDR3 of light chain of C0812 antibody

<400> SEQUENCE: 31

Ser Gln Ser Thr His Val Pro Tyr Thr
1               5

<210> SEQ ID NO 32
<211> LENGTH: 5
<212> TYPE: PRT
<213> ORGANISM: artificial sequence
<220> FEATURE:
<223> OTHER INFORMATION: CDR1 of heavy chain of C0815 antibody

<400> SEQUENCE: 32

Asp Tyr Ser Met His
1               5

<210> SEQ ID NO 33
<211> LENGTH: 17
<212> TYPE: PRT
<213> ORGANISM: artificial sequence
<220> FEATURE:
<223> OTHER INFORMATION: CDR2 of heavy chain of C0815 antibody

<400> SEQUENCE: 33

Trp Ile Asn Thr Glu Thr Gly Lys Pro Thr Tyr Ala Asp Asp Phe Lys
1               5                   10                  15

Gly

<210> SEQ ID NO 34
<211> LENGTH: 3
<212> TYPE: PRT
```

-continued

```
<213> ORGANISM: artificial sequence
<220> FEATURE:
<223> OTHER INFORMATION: CDR3 of heavy chain of C0815 antibody

<400> SEQUENCE: 34

Leu Asp Tyr
1

<210> SEQ ID NO 35
<211> LENGTH: 16
<212> TYPE: PRT
<213> ORGANISM: artificial sequence
<220> FEATURE:
<223> OTHER INFORMATION: CDR1 of light chain of C0815 antibody

<400> SEQUENCE: 35

Arg Ser Ser Gln Asn Val Val His Ser Ser Gly Asn Thr Tyr Leu Glu
1               5                   10                  15

<210> SEQ ID NO 36
<211> LENGTH: 7
<212> TYPE: PRT
<213> ORGANISM: artificial sequence
<220> FEATURE:
<223> OTHER INFORMATION: CDR2 of light chain of C0815 antibody

<400> SEQUENCE: 36

Lys Val Ser Asn Arg Phe Ser
1               5

<210> SEQ ID NO 37
<211> LENGTH: 9
<212> TYPE: PRT
<213> ORGANISM: artificial sequence
<220> FEATURE:
<223> OTHER INFORMATION: CDR3 of light chain of C0815 antibody

<400> SEQUENCE: 37

Phe Gln Gly Ser His Val Pro Tyr Thr
1               5
```

What is claimed is:

1. A monoclonal antibody that binds specifically to a protein having the same amino acid sequence as sequence No. 1 or a partial peptide of the protein, recognizing an epitope presented in an amino acid sequence of sequence No. 6, comprising a CDR1, CDR2 and CDR3 of an antibody H chain V region having the amino acid sequences set forth in SEQ ID NOS:20, 21, and 22, respectively; and a CDR1, CDR2 and CDR3 of an antibody L chain V region having the amino acid sequences set forth in SEQ ID, NOS:23, 24 and 25, respectively.

2. The monoclonal antibody according to claim 1, which is an IgG1.

3. A monoclonal antibody that binds specifically to a protein having the same amino acid sequence as sequence No. 1 or a partial peptide of the protein, recognizing an epitope presented in an amino acid sequence of sequence No. 6which is an antibody produced by hybridoma accession No. NITE BP-668.

4. A hybridoma of accession No. NITE BP-668.

5. A tumor diagnostic agent comprising as an active ingredient the monoclonal antibody according to claim 1 bound to a detectable label enabling detection, and wherein the antibody binds specifically with human GPR87.

6. The tumor diagnostic agent according to claim 5, wherein the detectable label is a radioisotope label and the tumor diagnostic agent can be used as a tumor diagnostic agent for PET.

7. A tumor therapeutic agent comprising as an active ingredient the monoclonal antibody according to claim 1, wherein the monoclonal antibody has cellular cytotoxic activity.

8. A tumor therapeutic agent comprising, as an active ingredient, a monoclonal antibody according to claim 1 that has been conjugated with a cytotoxic substance.

9. A tumor diagnostic agent comprising the monoclonal antibody of claim 1 that binds specifically with GPR87 on a GPR8-expressing tumor cell of a tumor selected from the group consisting of skin cancers, head and neck cancers, lung cancers, esophageal cancers, cervical cancers, uterine cancers, pancreatic cancers, breast cancers, kidney cancers, ureteral cancers, and bladder cancers.

10. A tumor therapeutic agent for treating a tumor comprising, as an active ingredient, the monoclonal antibody of claim 1 that binds specifically with GPR87, wherein the tumor is selected from the group consisting of skin cancers, head and neck cancers, lung cancers, esophageal cancers, cervical cancers, uterine cancers, pancreatic cancers, breast cancers, kidney cancers, ureteral cancers, and bladder cancers.

11. The tumor therapeutic agent of claim 10, wherein the tumor is selected from the group consisting of prickle cell carcinomas, basal cell carcinomas, melanomas of skin, tongue cancers, squamous cell carcinomas, malignant lymphomas of a pharynx, squamous cell carcinomas of a larynx, squamous cell carcinomas, small cell carcinomas of a lung, squamous cell carcinomas of an esophagus, squamous cell carcinomas of a cervix, uterine adenocarcinomas, transitional cell carcinomas, squamous cell carcinomas of a bladder, and transitional cell carcinomas of a renal pelvis or ureters.

12. Method of determining the presence of an antigen comprising contacting a sample comprising protein, cells or tissue with the antibody according to claim 1, and determining whether the antibody binds to the sample.

13. The method according to claim 12, further comprising determining whether GPR87 is expressed to determine whether the sample comprises tumor cells.

14. The method according to claim 12, wherein the sample comprises breast tissue and determining whether GPR87 is expressed to determine whether cancer cells are present.

* * * * *